(12) United States Patent
Ewald et al.

(10) Patent No.: US 11,938,183 B2
(45) Date of Patent: Mar. 26, 2024

(54) AUTOIMMUNE ANTIBODIES FOR USE IN INHIBITING CANCER CELL GROWTH

(71) Applicant: The Johns Hopkins University, Baltimore, MD (US)

(72) Inventors: Andrew J. Ewald, Catonsville, MD (US); Veena Padmanaban, Baltimore, MD (US); Livia Casciola-Rosen, Pikesville, MD (US); Antony Rosen, Pikesville, MD (US)

(73) Assignee: The Johns Hopkins University, Baltimore, MD (US)

( * ) Notice: Subject to any disclaimer, the term of this patent is extended or adjusted under 35 U.S.C. 154(b) by 38 days.

(21) Appl. No.: 17/366,635

(22) Filed: Jul. 2, 2021

(65) Prior Publication Data

US 2022/0160868 A1 May 26, 2022

Related U.S. Application Data

(63) Continuation of application No. 15/573,323, filed as application No. PCT/US2016/031827 on May 11, 2016, now abandoned.

(60) Provisional application No. 62/159,696, filed on May 11, 2015.

(51) Int. Cl.
| | |
|---|---|
| *A61K 39/00* | (2006.01) |
| *A61K 39/395* | (2006.01) |
| *C07K 16/06* | (2006.01) |
| *C07K 16/18* | (2006.01) |
| *C07K 16/28* | (2006.01) |
| *C07K 16/30* | (2006.01) |
| *G01N 33/50* | (2006.01) |
| *G01N 33/564* | (2006.01) |
| *G01N 33/574* | (2006.01) |
| *C07K 16/40* | (2006.01) |

(52) U.S. Cl.
CPC ............ *A61K 39/395* (2013.01); *C07K 16/06* (2013.01); *C07K 16/18* (2013.01); *C07K 16/2863* (2013.01); *C07K 16/30* (2013.01); *G01N 33/5011* (2013.01); *G01N 33/5029* (2013.01); *G01N 33/564* (2013.01); *G01N 33/574* (2013.01); *A61K 2039/505* (2013.01); *C07K 16/40* (2013.01)

(58) Field of Classification Search
None
See application file for complete search history.

(56) References Cited

U.S. PATENT DOCUMENTS

| | | |
|---|---|---|
| 3,710,795 A | 1/1973 | Higuchi et al. |
| 4,485,045 A | 11/1984 | Regen |
| 4,544,545 A | 10/1985 | Ryan et al. |
| 4,863,457 A | 9/1989 | Lee |
| 4,868,116 A | 9/1989 | Morgan et al. |
| 4,980,286 A | 12/1990 | Morgan et al. |
| 5,013,556 A | 5/1991 | Woodle et al. |
| 5,223,409 A | 6/1993 | Ladner et al. |
| 5,403,484 A | 4/1995 | Ladner et al. |
| 5,427,908 A | 6/1995 | Dower et al. |
| 5,501,856 A | 3/1996 | Ohtori et al. |
| 5,508,717 A | 4/1996 | Miller |
| 5,571,698 A | 11/1996 | Ladner et al. |
| 5,780,279 A | 7/1998 | Matthews et al. |
| 5,811,097 A | 9/1998 | Allison et al. |
| 5,855,887 A | 1/1999 | Allison et al. |
| 5,993,818 A | 11/1999 | Torchilin et al. |
| 6,005,079 A | 12/1999 | Casterman et al. |
| 6,040,136 A | 3/2000 | Garrard et al. |
| 6,051,227 A | 4/2000 | Allison et al. |
| 6,984,720 B1 | 1/2006 | Korman et al. |
| 7,390,786 B2 | 6/2008 | Warne et al. |
| 7,521,051 B2 | 4/2009 | Collins et al. |
| 8,552,154 B2 | 10/2013 | Freeman et al. |
| 2005/0201994 A1 | 9/2005 | Korman et al. |
| 2008/0241223 A1 | 10/2008 | Nivaggioli et al. |
| 2014/0336282 A1* | 11/2014 | Ewald ............ G01N 33/57415 435/7.1 |

FOREIGN PATENT DOCUMENTS

| | | |
|---|---|---|
| EP | 0430539 | 6/1991 |
| EP | 488401 | 8/1991 |
| EP | 1212422 | 2/2020 |
| WO | WO 1994/04678 | 3/1944 |
| WO | WO 1988/06630 | 9/1988 |
| WO | WO 1989/02468 | 3/1989 |
| WO | WO 1989/05345 | 6/1989 |
| WO | WO 1989/07136 | 8/1989 |
| WO | WO 1992/07573 | 5/1992 |
| WO | WO 1992/15679 | 9/1992 |
| WO | WO 1994/25591 | 11/1994 |
| WO | WO 1997/08320 | 3/1997 |
| WO | WO 2001/014424 | 3/2001 |
| WO | WO 2004/035607 | 6/2004 |
| WO | WO 2004/060407 | 6/2004 |
| WO | WO 2007/084321 | 11/2007 |
| WO | WO 2009/137832 | 11/2009 |
| WO | WO 2010/036959 | 4/2010 |
| WO | WO 2013/079174 | 6/2013 |

OTHER PUBLICATIONS

Alarcon-Segovia et al., ."Antibody to nuclear ribonucleoprotein penetrates live human mononuclear cells through Fc receptors," Nature, 1978, 271:67-69.

Alarcon-Segovia et al.. "The recovery of self tolerance in SLE," Lupus, 2001, 10:521-522.

Allison et al., "Molecular pathology of breast cancer: what a pathologist needs to know," Am J Clin Pathol., 2012, 138:770-780.

(Continued)

*Primary Examiner* — G. R. Ewoldt
(74) *Attorney, Agent, or Firm* — Fish & Richardson P.C.

(57) ABSTRACT

The present disclosure provides, among other things, compositions (e.g., autoantibodies) that inhibit the growth, viability, or mobility of (invasion by) a cancer cell. Also provided are applications, such as therapeutic and diagnostic methods, in which the agents are useful, as well as screening methods for identifying autoantibodies useful in the applications.

17 Claims, 17 Drawing Sheets

(56) References Cited

OTHER PUBLICATIONS

Armentano et al., "Expression of human factor IX in rabbit hepatocytes by retrovirus-mediated gene transfer: potential for gene therapy of hemophilia B.," Proc. Natl. Acad. Sci. USA, 1990, 87(16):6141-6145.
Avrameas et., Natural autoantibodies: from 'horror autotoxicus' to 'gnothi seauton' Immunol Today, 1991, 12:154-159.
Berge et al., "Pharmaceutical Salts," J Pharm Sci., 1977, 66:1-19.
Berkner et al., "Development of adenovirus vectors for the experssion of heterologous genes.," (1988) Bio Techniques 6(7):616.
Bernatsky et al., "Breast, ovarian, and endometrial malignancies in systemic lupus erythematosus: a meta-analysis," Br J Cancer, 2011, 104: 1478-1481.
Berry et al., Effect of screening and adjuvant therapy on mortality from breast cancer. N Engl J Med (2005) 353, 1784-1792.
Blixt et al., "Autoantibodiesto aberrantly glycosylated MUCI in early stage breast cancer are associated with a better prognosis," Breast Cancer Res,. 2011 13(R25):1-16.
Burnet et al., "Cancer: a biological approach. III. Viruses associated with neoplastic conditions. IV. Practical applications," Br Med J 1, 1957, 841-847.
Chaffer et al., "A perspective on cancer cell metastasis," Science, 2011, 331:1559-1564.
Cheung et al., "Collective invasion in breast cancer requires a conserved basal epithelial program," Cell, 2013, 155:1639-1651.
Chinoy, et al., Interferon-gamma and interleukin-4 gene polymorphisms in Caucasian idiopathic inflammatory myopathy patients in UK ___ Ann Rheum Dis (2007) 66:970-973.
Chowdhury et al. "Long-Term Improvement of Hypercholesterolenia After ex Vivo Gene Therapy in LDLR-Deficient Rabbits," Science, 1991, 254:1802-1805.
Cohen, "Discrimination and dialogue in the immune system," Semin Immunol., 2000, 12, 215-219; discussion 257-344.
Cohen et al., Natural autoanlibodies might prevent autoimmune disease ___ Immunol Today (1986) 7:363-364.
Cooper et al., "Linking environmental agents and autoimmune diseases," Environ Health Perspect, 1999, 107 Suppl 5, 659-660.
Coutinho, et al, Natural autoanlibodies ___ Curr Opin Immunol (1995) 7, 812-818.
Daffa, et al, "Natural and disease-specific autoantibodies in chronic obstructive pulmonary disease,"Clin Exp Immunol (2015) 180:155-163.
Dai et al. "Gene therapy via primary myoblasts: Long-term expression of factor IX protein following transplantation in vivo," Proc Natl Acad Sci USA, 1992, 89:10892-10895;.
Danke, et al, Autoreactive T cells in healthy individuals. J Immunol (2004) 172:5967-5972.
Danos and Mulligan "Safe and efficient generation of recombinant retroviruses with amphotropic and ecotropic host ranges," Proc Natl Acad Sci USA, 1988, 85:6460-6464.
Davis et al. Transgenic mice as a source of fully human antibodies for the treatment of cancer. Cancer Metastasis Rev (1999); 18: 421-425.
De La Cruz et al. Immunogenicity and epitope mapping of foreign sequences via genetically engineered llamentous phage. J Biol Chem (1988); 263: 4318-4322.
Dunn, et al, Cancer immunoediting: from immunosurveillance to tumor escape ___ Nat Immunol (2002) 3:991-998.
Eglitis et al. Gene expression in mice after high efficiency retroviral-mediated gene transfer. Science (1985}; 230:1395-1398.
Ehrenstein, et al, The importance of natural lgM: scavenger, protector and regulator ___ Nat Rev Immunol {2010) 10:1778-786.
Encinas, et al, Mapping and identification of autoimmunity genes_ Curr Opin Immunol (2000) 12:691-697.
Eppstein et al.et al., Biological activity of liposome-encapsulated murine interferon gamma is mediated by a cell membrane receptor. Proc Nall Acad Sci USA (1985); 82: 3688-3692.

Ewald, et al, Collective epithelial migration and cell rearrangements drive mammary branching morphogenesis Dev Cell (2008) 14:570-581.
Ferry et al. Retroviral-mediated gene transfer into hepatocytes in vivo. Pree Natl Acad Sci USA 1991, 68:8377-8381.
Filion et al., Presence in peripheral blood of healthy individuals of autoreactive T cells to a membrane antigen present on bone marrow-derived cells. Blood (1996) 88:2144-2150.
Fiorentino, et al., Most patients with cancer-associated dermatomyositis have antibodies to nuclear matrix protein NXP-2 or transcription intermediary factor 1gamma. Arthritis Rheum (2013) 65:2954-2962.
Fleming, et al., The pathology of scleroderma vascular disease. Rheum Dis Clin North Am (2008) 34, 41-55; vi.
Flotte et al. Gene Expression from Adena-associated Virus Vectors in Airway Epithelial Cells. Am J Respir Cell Mol Biol (1992); 7: 349-356.
Friedl, et al., Classifying collective cancer cell invasion. Nat Cell Biol (2012) 14, 777-783.
Friedl, et al., Collective cell migration in morphogenesis, regeneration and cancer. Nat Rev Mal Cell Biol (2009); 10:445-457.
Furst, et al., Epidemiology of adult idiopathic inflammatory myopathies in a U.S. managed care plan. Muscle & Nerve (2012); 45: 676-683.
Furst, et al., Medical costs and health-care resource use in patients with inflammatory myopathies in an insured Population. Muscle Nerve (2012) 46, 496-505.
Gene "Antibody-selectable filamentous fd phage vectors: affinity purification of target genes," Elsevier, 1988, 73 :305-318.
Golan, et al., Penetration of autoantibodies into living epithelial cells. J Invest Dermatol (1993) 100, 316-322.
Grabar, Hypothesis_Auto-antibodies and immunological theories: an analytical review. Clin Immunol Immunopathol (1975) 4, 453-466.
Hanahan, D., and Weinberg, R.A. (2011). Hallmarks of cancer: the next generation. Cell 144, 646-674.
Hanauske et al. Phase 1 b Dose Escalation Study of Erlotinib in Combination with infusional 5—Fluorouracil, Leucovorin, and Oxaliplalin in Patients with Advanced Solid Tumors. Clin Cancer Res (2007); 13: 523-531.
Hanauske, et al., Phase 1 b Dose Escalation Study of Erlotinib in Combination with infusional 5-Fluorouracil, Leucovorin, and Oxaliplatin in Patients with Advanced Solid Tumors. Clin Cancer Res (2007); 13: 523-531.
Hansen et al., "Targeting cancer with a lupus autoantibody.", Sci Transl Med 4(157): 157ra142, 2012.
Hetherington et al .Phase I Dose Escalation Study To Evaluate the Safety and Pharmacokinetic Profile of Tefetibazumab in Subjects with End-Stage Renal Disease Requiring Hemodialysis. Antimicrobial Agents and Chemotherapy (2006); 50: 3499-3500.
Hill, et al., Frequency of specific cancer types in dermatomyositis and polymyositis: a population-based study ___ Lancet (2001) 357, 96-100.
Huber et al. Retroviral-mediated gene therapy for the treatment of hepatocellular carcinoma: an innovative approach for cancer therapy ___ Proc Nall Acad Sci USA (1991 ); 88: 8039-8043.
Hudson, et al., High avidity scFv multimers; diabodies and triabodies. J Immunol Methods (1999); 231: 177-189.
Hwang et al. Hepatic uptake and degradation of unilamellar sphingomyelin/cholesterol liposomes: a kinetic study, Proc Natl Acad Sci USA (1980); 77: 4030-4034.
Hwu et al. Functional and molecular characterization of tumor-infiltrating lymphocytes transduced with tumor necrosis factor-alpha cDNA for the gene therapy of cancer in humans. J Immunol (1993); 150:4104-4115.
Invernizzi, The X chromosome in female-predominant autoimmune diseases. Ann NY Acad Sci (2007) 1110, 57-64.
Ippolito, et al., Autoantibodies in systemic lupus erythematosus: comparison of historical and current assessment of seropositivity. Lupus (2011) 20, 250-255.
Jemal et al., Cancer statistics, 2010. CA Cancer J Clin (2010) 60, 277-300.

(56) References Cited

OTHER PUBLICATIONS

Joseph, et al., Association of the autoimmune disease scleroderma with an immunologic response to cancer. Science (2014) 343, 152-157.
Kalbasi, et al., Radiation and immunotherapy: a synergistic combination. JCL (2013); 123: 2756.
Kay et al. Hepatic Gene Therapy: Persistent Expression of Human al-Antitrypsin in Mice after Direct Gene Delivery n Vwo. Human Gene Therapy (1992); 3:641-647.
Kyewski, et al., A central role for central tolerance. Annu Rev Immunol (2006) 24, 571-606.
Lacroix-Desmazes, el al., Self-reactive antibodies {natural autoantibodies) in healthy individuals. J Immunol Methods { 1998) 216, 117-137.
Leighton, et al., Phatogenesis of tumor invasion. II. Aggregate replication. Cancer Res (1960) 20, 575-586.
Lu, et al., Breast cancer metastasis: challenges and opportunities. Cancer Res {2009) 69, 4951-4953.
Madrid, et al., Serologic laboratory findings in malignancy. Rheum Dis Clin North Am (2011) 37, 507-525.
Mammen, Dermatomyositis and polymyositis: Clinical presentation, autoantibodies, and pathogenesis. Ann NY Acad Sci (2010) 1184, 134-153.
Margolese et al., Mastectomy or lumpectomy? The choice of operation for clinical stages I and II breast cancer, The Steering Committee on Clinical Practice Guidelines For The Treatment of Breats Cancer, Mastectomy or lumpectomy? The choice of operation for clinical stages I and II breast cancer. CMAJ (1998) 158 Suppl 3, S15-21.
Mathe, et al., Passive, adoptive, and active immunotherapy: a review of clinical trials in cancer. Cancer Detect Prev (1987) Suppl 1, 279-290.
Mayes, et al., Prevalence, incidence, survival, and disease characteristics of systemic sclerosis in a large US population. Arthritis Rheum (2003) 48, 2246-2255.
McLaughlin et al. Adena-associated virus general transduction vectors: analysis of proviral structures. J Virol 1988); 62: 1963-1973.
Melero, J., Tarrago, D., Nunez-Roldan, A., and Sanchez, B. (1997). Human polyreactive IgM monoclonal antibodies with blocking activity against self-reactive IgG. Scand J Immunol 45, 393-400.
Miller, Biological rationale for endocrine therapy in breast cancer. Best Pract Res Clin Endocrinol Metab (2004) 18,1-32.
Moinzadeh, et al., Association of anti-RNA polymerase III autoantibodies and cancer in scleroderma. Arthritis Research and Therapy (2014); 16: R53.
Munoz et al., The role of defective clearance of apoptotic cells in systemic autoimmunity. Nat Rev Rheumatol (2010) p. 280-289.
Muramatsu et al, Specific expression of activation-induced cytidine deaminase (AID), a novel member of the RNAediting deaminase family in germinal center B cells. J Biol Chem (1999) 274, 18470-18476.
Muyldermans et al. Recognition of antigens by single-domain antibody fragments: the superfluous luxury of baired domains. Trends Biochem Sci (2001); 26: 230-235.
Nagele, et al., Natural lgG Autoantibodies Are Abundant and Ubiquitous in Human Sera, and Their Number Is Influenced By Age, Gender, and Disease. PLoS ONE (2013); 8: e60726.
Nguyen-Ngoc, K.V., Cheung, K.J., Brenot, A., Shamir, E.R., Gray, R.S., Hines, W.C., Yaswen, P., Werb, Z., and Ewald, A.J. (2012). ECM microenvironment regulates collective migration and local dissemination in normal and malignant mammary epithelium. Proc Natl Acad Sci US A 109, E2595-2604.
[No Author], "Anti-TIF1-γ ELISA Kit", MBL, Cat No. 7853 R, 7 pages, 2017.
Noble et al, A nucleolytic lupus autoantibody is toxic to BRCA2-deficient cancer cells. Sci Rep (2014) 4, 5958.
Noseworthy, et al., Multiple sclerosis. N Engl J Med (2000) 343, 938-952.

Nuttall et al. Immunoglobulin VH Domains and Beyond Design and Selection of Single-Domain Binding and irargeting Reagents Curr Pharm Biotech (2000); 1: 253-263.
Ochsenbein et al, Control of early viral and bacterial distribution and disease by natural antibodies. Science (1999)286, 2156-2159.
Ohashi T-cell signalling and autoimmunity: molecular mechanisms of disease ___ Nat Rev Immunol (2002); 2: 427-438.
Pardoll, Immunology beats cancer: a blueprint for successful translation. Nat Immunol (2012) 13, 1129-1132.
Parish, Cancer immunolherapy: the past, the present and the future. Immunol Cell Biol (2003) 81, 106-113.
Poljak Production and structure of diabodies. Structure (1994); 2: 1121-1123.
Reichmann et al. Single domain antibodies: comparison of camel VH and camelised human VH domains. J Immunol Meth (1999); 231: 25-38.
Rioux, et al., Paths to understanding the genetic basis of autoimmune disease. Nature (2005); 435: 584-589.
Rondon Intracellular antibodies (intrabodies) for gene therapy of infectious diseases. Annu Rev Microbial (1997); 51 : 257-283.
Rosenfeld et al In vivo transfer of the human cystic fibrosis transmembrane conductance regulator gene to the airway epit1 lelium. Cell (1992); 68: 143-155.
Rosenfeld et al. Adenovirus-mediated transfer of a recombinant otl-antitrypsin gene to the lung epithelium in vivo. Science ( 1991); 252: 431-434.
Sahai, Illuminating the metastatic process. Nat Rev Cancer (2007) 7, 737-749.
Samulski et al.Helper-free stocks of recombinant adeno-associated viruses: normal integration does not require viral gene expression J Viral (1989); 63: 3822-3826.
Schreiber el al., Cancer immunoediting: integrating immunity's roles in cancer suppression and promotion. Science (2011)331, 1565-1570.
Seddon, et al., The third function of the thymus. Immunol Today (2000) 21, 95-99.
Seidel, el al., Natural killer cell mediated antibodydependent cellular cytotoxicity in tumor immunotherapy with therapeutic antibodies. Front Immunol (2013) 4, 76.
Shah et al., Close temporal relationship between onset of cancer and scleroderma in patients with RNA polymerase I/III antibodies. Arthritis Rheum (2010) 62, 2787-2795.
Shah, et al., Examination of autoantibody status and clinical features associated with cancer risk and cancer-associated scleroderma. Arthritis Rheumatol (2015) 67, 1053-1061.
Shamir, el al., Three-dimensional organotypic culture: experimental models of mammalian biology and disease. Nat Rev Mal Cell Biol (2014) 15, 647-664.
Simian, et al., The interplay of matrix metalloproleinases, morphogens and growth factors is necessary for branching of mammary epithelial cells. Development (2001) 128, 3117-3131.
Sinha, et al., Autoimmune diseases: the failure of self tolerance. Science (1990) 248, 1380-1388.
Smith et al., Filamentous fusion phage: novel expression vectors that display cloned antigens on the virion surface. Science (1985); 228: 1315-1317.
Somers, et al., Population-based incidence and prevalence of systemic lupus erythematosus: the Michigan Lupus Epidemiology and Surveillance program. Arthritis Rheumatol (2014) 66, 369-378.
Soussi, p53 Antibodies in the sera of patients with various types of cancer: a review. Cancer Res (2000) 60, 1777-1788.
Street, et al., Perforin and interferongamma activities independently control tumor initiation, growth, and metastasis_Blood (2001) 97, 192-197.
Stutman, "Immunodepression and malignancy.", Adv Cancer Res 22, 261-422, 1975.
Taylor et al. A transgenic mouse that expresses a diversity of human sequence heavy and light chain mmunoglobulins. Nudeic Acids Res (1992); 20: 6287-6295.
Tevaarwerk, et al., Survival in patients with metastatic recurrent breast cancer after adjuvant chemotherapy: little evidence of improvement over the past 30 years ___ Cancer (2013) 119, 1140-1148.

(56) References Cited

OTHER PUBLICATIONS

Tinoco, G., Warsch, S., Gluck, S., Avancha, K., and Montero, A.J. (2013). Treating breast cancer in the 21st century: emerging biological therapies. J Cancer 4, 117-132.

Todorovska et al. Design and application of diabodies, triabodies and tetrabodies for cancer targeting. J Immunol Methods (2001); 248: 47-66.

Tomer, Y., and Shoenfeld, Y. (1988). The significance of natural autoantibodies. Immunol Invest 17, 389-424.

Tomizuka et al. Double trans-chromosomic mice: maintenance of two individual human chromosome fragments containing Ig heavy and kappa loci and expression offully human antibodies. Pree Natl Acad Sci USA (2000); 97:722-727.

Van Beusechem et al. .Long-term expression of human adenosine deaminase in rhesus monkeys transplanted wilt retrovirus-infected bone-marrow cells. Proc Natl Acad Sci (1992); 89: 7640-7644.

Van Gurp et al. Phase 1 Dose-Escalation Study of CP-690 550 in Stable Renal Allograft Recipients: Preliminary Findings of Safety, Tolerability, Effects on Lymphocyte Subsets and Pharmacokinetics. Am J Transplantation (2008);8:1711-1718.

Vargo-Gogola, T., and Rosen, J.M. (2007). Modelling breast cancer: one size does not fit all. Nat Rev Cancer 7, 659-672.

Walker, L.S., and Abbas, A.K. (2002). The enemy within: keeping self-reactive T cells at bay in the periphery. Nat Rev Immunol2, 11-19.

Weiner, et al., Monoclonal antibodies: versatile platforms for cancer immunotherapy. Nat Rev Immunol (2010); 10: 617-327.

Wilson et al. Retrovirus-mediated transduction of adult hepatocytes. Pree Nall Acad Sci (1988}; 85: 3014-3018.

Onitilo et al., "Breast Cancer Subtypes Based on ER/PR and Her2 Expression: Comparison of Clinicopathologic Features and Survival," Jun. 2009, Clinical Medicine & Research, 7(1/2):4-13.

\* cited by examiner

DIGEST FRESH TUMOR SPECIMEN → GENERATE ORGANOIDS → EMBED IN 3D COLLAGEN | GEL → MONITOR INVASION

| DISEASE | TOTAL NUMBER OF ANTISERA | NUMBER OF ANTISERA THAT STAINED TUMOR ORGANOIDS | NUMBER OF ANTISERA THAT STAINED NORMAL ORGANOIDS |
|---|---|---|---|
| DERMATOMYOSITIS | 4 | 3 | 4 |
| SCLERODERMA | 9 | 4 | 8 |
| LUPUS | 5 | 3 | 5 |

| SNO. | SERUM (IgG) # | DISEASE | AUTOANTIBODIES | TUMOR | | NORMAL | |
|---|---|---|---|---|---|---|---|
| | | | | INTENSITY OF CYTOPLASMIC STAINING | INTENSITY OF NUCLEAR STAINING | INTENSITY OF CYTOPLASMIC STAINING | INTENSITY OF NUCLEAR STAINING |
| 1 | LCR | CONTROL | NONE | - | - | + | - |
| 2 | C19 | CONTROL | NONE | - | - | ++ | - |
| 3 | SLE 2055 | LUPUS | Ro52 + La | ++ | ++ | ++ | ++ |
| 4 | FW-1366 | SCLERODERMA | RNA POLYMERASE III | ++ | ++ | ++ | ++ |
| 5 | 13,040 | MYOSITIS | Ro52 + Jo1 | ++ | - | ++ | - |
| 6 | 13,200 | MYOSITIS | NXP2 | ++ | - | - | - |
| 7 | SLE 1269 | LUPUS | DNA+Sm+RNP+Ro52+La | ++ | - | ++ | ++ |
| 8 | 13,142 | MYOSITIS | Mi2 | + | + | ++ | ++ |
| 9 | FW-1965 | SCLERODERMA | RNA POLYMERASE III | + | + | + | + |
| 10 | 12,106 | MYOSITIS | TIF1gamma | + | + | - | + |
| 11 | SLE 1172 | LUPUS | DNA+Sm+RNP | + | - | + | + |
| 12 | FW-1402 | SCLERODERMA | CENTROMERE | + | - | + | - |
| 13 | 13,019 | MYOSITIS | MDA5 | - | - | + | - |
| 14 | 12,094 | MYOSITIS | TIF1gamma | - | - | + | - |
| 15 | 13,070 | MYOSITIS | MDA5 | - | - | + | - |
| 16 | RFW-0042 | SCLERODERMA | TOPOISOMERASE 1 | - | - | ++ | + |
| 17 | FW-1990 | SCLERODERMA | TOPOISOMERASE 1 | - | - | ++ | - |
| 18 | SLE 1246 | LUPUS | DNA+Sm+RNP | - | - | ++ | - |
| 19 | 13,195 | MYOSITIS | Mi2 | - | - | + | - |
| 20 | 13,093 | MYOSITIS | NXP2 | - | - | + | - |

*FIG. 2C*

| CULTURE CONDITION | % CYTOTOXICITY | | % INVASIVE ORGS | | % DECREASE IN INVASION | |
|---|---|---|---|---|---|---|
| | TUMOR #1 | TUMOR #2 | TUMOR #1 | TUMOR #2 | TUMOR #1 | TUMOR #2 |
| DAY 0 | 0.0 | 0.0 | 0.0 | 0.0 | - | - |
| DAY 6 | 0.0 | 0.0 | 33.3 | 8.3 | - | - |
| C3 | 0.0 | 0.0 | 56.3 | 30.0 | - | - |
| C34 | 0.0 | 4.2 | 41.2 | 25.0 | - | - |
| SLE1269 | 10.0 | 0.0 | 55.0 | 5.9 | 2.3 | 80.4 |
| FW1366 | 4.8 | 0.0 | 57.1 | 31.6 | -1.5 | -5.3 |
| 13200 | 4.2 | 0.0 | 12.5 | 8.7 | 77.8 | 71.0 |
| 12106 | 17.4 | 5.9 | 26.1 | 11.8 | 53.7 | 60.8 |

EFFECT OF AUTOANTIBODIES (OBTAINED FROM PATIENTS WITH A KNOWN CANER STATUS) ON TUMOR INVASION IN 3D CULTURE

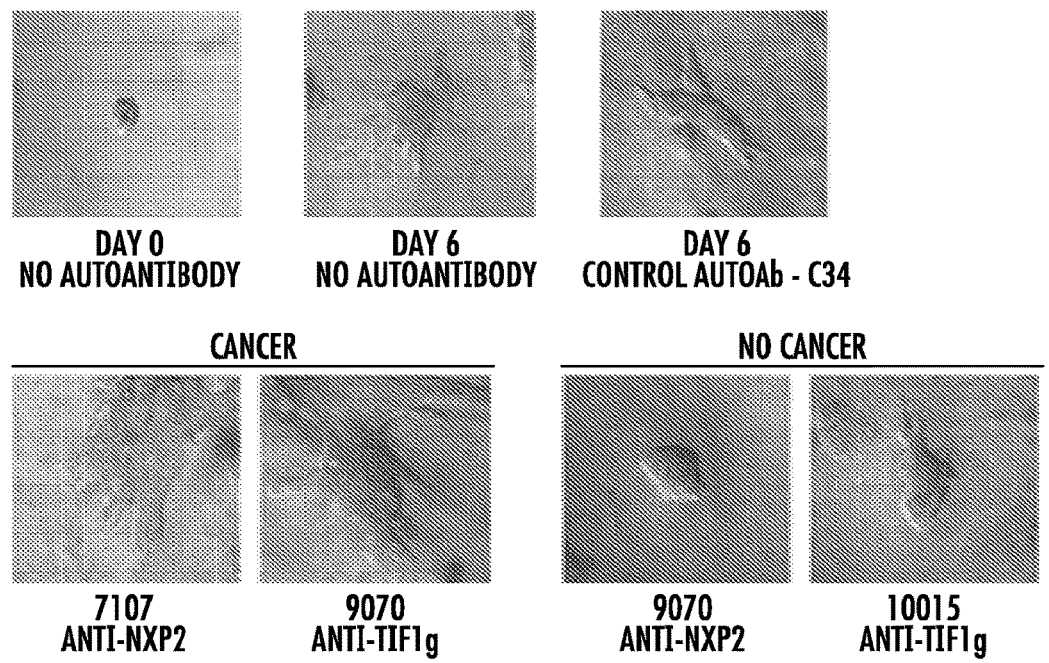

FIG. 8A

| CULTURE CONDITION | TOTAL NO. OF ORGANOIDS | NUMBER OF ORGANOIDS | | | | | % NON-INVASIVE | % INVASIVE | %DEAD ORGS |
|---|---|---|---|---|---|---|---|---|---|
| | | SCORE=3 | SCORE=2 | SCORE=1 | SCORE=0 | SCORE=b | | | |
| DAY 6 (NO Ab) | 50 | 6 | 4 | 6 | 29 | 1 | 70.0 | 20.0 | 8.0 |
| CONTROL Ab C3 | 39 | 5 | 3 | 3 | 26 | 1 | 74.4 | 20.5 | 2.6 |
| 7107 (C) | 43 | 5 | 4 | 4 | 28 | 0 | 74.4 | 20.9 | 4.7 |
| 9070 (C) | 40 | 7 | 3 | 2 | 24 | 0 | 65.0 | 25.0 | 10.0 |
| 9109 (NC) | 33 | 1 | 3 | 3 | 24 | 0 | 81.8 | 12.1 | 6.1 |
| 10015 (NC) | 38 | 5 | 2 | 3 | 25 | 0 | 73.7 | 18.4 | 7.9 |

KEY: ORGANOIDS WERE ASSIGNED AN INVASION SCORE OF 0-3 BASED ON THE NUMBER OF PROTRUSIVE STRANDS THEY EXTEND INTO COLLAGEN; D: DEAD ORGANOIDS;B: NOT ANALYZABLE. ORGANOIDS WITH A SCORE OF 0-1 AND 2-3 WERE GROUPED AS NON-INVASIVE AND INVASIVE RESPECTIVELY. NC, C:Ab ISOLATED FROM PATIENT WITH NO CANCER AND CANCER RESPECTIVELY.

AUTOIMMUNE ANTIBODIES FOR USE IN INHIBITING CANCER CELL GROWTH

CROSS REFERENCE TO RELATED APPLICATIONS

This application is a continuation of U.S. application Ser. No. 15/573,323, filed Nov. 10, 2017, which is a 35 U.S.C. § 371 U.S. national stage entry of International Application No. PCT/US2016/031827, having an international filing date of May 11, 2016, which claims priority to U.S. Provisional Application No. 62/159,696, filed May 11, 2015, the contents of which are incorporated herein by reference in their entireties.

BACKGROUND

Despite the progress in understanding breast cancer development and progression, patients with metastatic breast cancer continue to have a five-year survival rate of 20%. Thus, there is an urgent need to better understand and treat metastasis.

SUMMARY

The present disclosure is based, at least in part, on the discovery that autoimmune antibodies inhibit cancer cell invasion. That is, the disclosure provides the results of experiments showing that antibodies from patients with autoimmune diseases specifically recognize antigens expressed in human breast tumors. These results indicate that autoantibodies may play a role in controlling tumor progression by targeting gene products (e.g., mutant gene products) associated with aberrant proliferation or cell invasion. Accordingly, the disclosure provides, among other things, a variety of compositions and methods useful for diagnostic, screening, and therapeutic applications relevant to cancer.

For example, in a first aspect, the disclosure provides a method for inhibiting a cancer cell. The method comprises contacting the cancer cell with an autoimmune antibody in an amount effective to inhibit the cancer cell. In some embodiments, the autoimmune antibody inhibits the growth of the cancer cell. In some embodiments, the autoimmune antibody inhibits the viability of the cancer cell. In some embodiments, the autoimmune antibody inhibits the mobility of the cancer cell. In some embodiments, the contacting occurs in vitro. In some embodiments, the contacting occurs in vivo. In some embodiments, the cancer cell can be, e.g., a lung cancer cell, breast cancer cell, colon cancer cell, pancreatic cancer cell, renal cancer cell, stomach cancer cell, liver cancer cell, bone cancer cell, hematological cancer cell, neural tissue cancer cell, melanoma, thyroid cancer cell, ovarian cancer cell, testicular cancer cell, prostate cancer cell, cervical cancer cell, vaginal cancer cell, or bladder cancer cell. In some embodiments, the cancer cell is contacted with more than one autoimmune antibody.

In some embodiments of any of the methods described herein, the cancer cell is contacted with blood or a blood fraction comprising one or more autoimmune antibodies. Blood fractions include, e.g., plasma and serum. In some embodiments of any of the methods described herein, the blood or blood fraction was obtained from a subject afflicted with lupus. In some embodiments, the blood or blood fraction was obtained from a subject afflicted with a dermatomyositis, scleroderma, rheumatoid arthritis, or multiple sclerosis.

In some embodiments of any of the methods described herein, the cancer cell is of the same histological type as one or more of the cells of the organ affected in the organ-specific autoimmune disease. For example, autoimmune antibodies to the skin or skin components may be useful for treating melanomas or other skin cancers. In some embodiments, autoantibodies reactive with normal lung may be used for treating lung cancers or inhibiting the growth of lung cancer cells.

In some embodiments, the autoantibody is from a subject having dermatomyositis and the cancer is a breast cancer (or the cancer cell is a breast cancer cell).

In some embodiments of any of the methods described herein, the autoimmune antibody is a monoclonal antibody. In some embodiments of any of the methods described herein, the antibody is an isolated and/or recombinant antibody. In some embodiments of any of the methods described herein, e.g., where blood or blood fraction products are used, a plurality of autoantibodies can be contacted to the cell, each antibody of different specificity (e.g., a polyclonal preparation).

In another aspect, the disclosure features a method for treating a subject afflicted with a cancer. The method comprises administering to the subject an autoimmune antibody in an amount effective to treat the cancer.

In some embodiments of any of the methods described herein, the subject is a human.

In some embodiments of any of the methods described herein, the cancer is, e.g., a lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, or bladder cancer.

In some embodiments of any of the methods described herein, more than one autoimmune antibody is administered to the subject.

In some embodiments of any of the methods described herein, a blood or a blood fraction comprising one or more autoimmune antibodies is administered to the subject.

In some embodiments, the blood or blood fraction was obtained from a subject afflicted with lupus or any other autoimmune disease described herein or known in the art. For example, the subject can have dermatomyositis, scleroderma, rheumatoid arthritis, or multiple sclerosis.

In some embodiments, the subject with autoimmune disease does not have a cancer. In some embodiments, the subject with autoimmune disease does have a cancer or had a cancer.

In some embodiments of any of the methods described herein, the autoantibody binds to a cell surface protein. In some embodiments of any of the methods described herein, the autoantibody binds to an intracellular antigen.

In yet another aspect, the disclosure features a method for identifying a compound (e.g., a small molecule, a nucleic acid, or an antibody) that inhibits a cancer cell. The method comprises: assaying in vitro the growth, viability, or mobility of a cancer cell in the presence of an antibody from a B cell obtained from a subject afflicted with an autoimmune disease, wherein a reduction in the growth, viability, or mobility of the cancer cell in the presence of the antibody, as compared to the growth, viability or mobility of the cancer cell in the absence of the antibody, identifies the antibody as an inhibitor of the cancer cell. In some embodiments of any of the methods described herein, the assaying step is run in the absence of a stromal cell population. In some embodiments, the assaying step is run in the presence of a stromal cell population. The stromal cell population may be selected from the group consisting of fibroblasts, T-cells, B-cells, dendritic cells, and eosinophils. In some embodiments of any of the methods described herein, the cancer cell is a group of cancer cells.

In another aspect, the disclosure features a screening method for identifying one or more antibodies that inhibit a cancer cell. The method comprises: assaying in vitro the growth, viability, or mobility of a cancer cell in the presence of each antibody of a plurality of antibodies from a subject afflicted with an autoimmune disease, wherein a reduction in the growth, viability, or mobility of the cancer cell in the presence of at least one of the antibodies, as compared to the growth, viability or mobility of the cancer cell in the absence of the antibody, identifies the antibody as an inhibitor of the cancer cell. In some embodiments of any of the methods described herein, the assaying step is run in the absence of a stromal cell population. In some embodiments, the assaying step is run in the presence of a stromal cell population. The stromal cell population may be selected from the group consisting of fibroblasts, T-cells, B-cells, dendritic cells, and eosinophils. In some embodiments of any of the methods described herein, the cancer cell is a group of cancer cells.

In another aspect, the disclosure features a method for identifying an autoimmune antibody that binds to a cancer cell or preparation of the cancer cell, the method comprising detecting the presence or absence of an interaction between an antibody and a cancer cell, wherein the antibody is from a subject afflicted with an autoimmune disease, wherein the presence of an interaction between the antibody and the cancer cell identifies the antibody as binding to the cancer cell.

In some embodiments of any of the methods described herein, the assaying or identification involves an organoid assay, such as one described and exemplified herein.

In some embodiments, any of the methods described herein further comprise determining that the antibody binds selectively to the cancer cell as compared to the binding of the antibody to a normal cell of the same histological type as the cancer cell. Suitable techniques include fluorescence assisted cell sorting (FACS) or immunoassay techniques, such as ELISA, Western blotting, or dot blotting.

In some embodiments, any of the methods described herein can include determining whether the antibody inhibits the growth, viability, or mobility of the cancer cell. Suitable methods for detecting inhibition of cell growth are described and exemplified herein. Cancer growth inhibition assays, migration assays, and apoptosis assays are also well known in the art.

In some embodiments, any of the methods described herein can further comprise determining whether the antibody selectively inhibits the growth, viability, or mobility of the cancer cell, as compared to the growth, viability, or mobility of a normal cell of the same histological type as the cancer cell. For example, the antibody can be assayed for any inhibitory or toxic effects on normal cells or in animals (e.g., non-human mammals or clinical studies in humans).

In some embodiments, any of the methods described herein can further comprise determining the antigen (e.g., the epitope or all or part of the protein, nucleic acid, or hapten) to which the antibody binds.

In some embodiments, any of the methods described herein further comprise isolating the antibody or a nucleic acid encoding the antibody from a B cell from the subject. In some embodiments, any of the methods described herein further comprise isolating the B cell from the subject.

In some embodiments, any of the methods described herein can further include producing the antibody in a non-human host cell comprising a nucleic acid encoding the antibody. The host cell can be a mammalian cell, such as a primate cell or a rodent cell (e.g., Chinese Hamster Ovary or NS0).

In yet another aspect, the disclosure features an antibody identified by any of the methods described herein, which antibody may be used in any of the methods described herein. In another aspect, the disclosure provides a blood product (comprising one or more autoimmune antibodies) for use in treating a cancer or inhibiting the growth, viability, or mobility of a cancer cell.

In some embodiments of any of the methods described herein, the antibody is a whole antibody. In some embodiments of any of the methods described herein, the antibody is an antigen-binding fragment of an antibody, such as an scFv, an Fd, a Fab, or a $F(ab')_2$. In some embodiments of any of the methods described herein, the autoantibody is from a human with autoimmune disease. In some embodiments, the antibody can be from a non-human mammal with an autoimmune disease, and, in such embodiments, the antibody can be humanized, chimerized, or de-immunized, prior to administration to a human.

In another aspect, the disclosure features a method for isolating cancer organoids, which comprises isolating a tumor from a host, generating organoids from the tumor, and embedding the organoids in collagen I (e.g., a 3-D fibrillar collagen I matrix). In another aspect, the disclosure provides a screening method for identifying a compound, such as an autoantibody, using the collagen embedded organoids. For example, the embedded organoids can be contacted with one or more (e.g., a plurality) of candidate compounds to determine whether such one or more compounds modulate (e.g., inhibit) the growth or invasion of the organoids.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for treating a subject with cancer, will be apparent from the following description, the examples, and from the claims.

BRIEF DESCRIPTION OF THE DRAWINGS

FIGS. 2A-2C. (2A) Schematic for immunofluorescence staining. Control 1: Staining with control antisera from normal patients, Control 2: Staining normal mammary organoids with all antisera. (2B) Distribution of the total number of autoantibodies among the various disease types, and fraction of positive staining with normal breast and tumor organoids. (2C) List of all antisera, disease type, known antibodies for each, and positivity of staining in the cytoplasm and nucleus against tumor and normal organoids. Positivity of staining was scored as −, + or ++.

FIGS. 8A-8D depict the effect of patient cancer-status on autoantibody-mediated decrease in tumor invasion. (8A) Representative DIC images depicting the invasion profile of tumor organoids collected on d0, or d6 without any autoantibody, or d6 with one of the following autoantibodies—7107, 9070, 9109, 10015 or C34 (control autoantibody). (8B) Table summarizing the invasion score, percentage invasion and cytotoxicity for each autoantibody (n=1 tumor). (8C) Bar graph comparing the effect of each autoantibody on invasion. (8D) Bar graph comparing the cytotoxicity of each autoantibody.

DETAILED DESCRIPTION

Figure 1A:
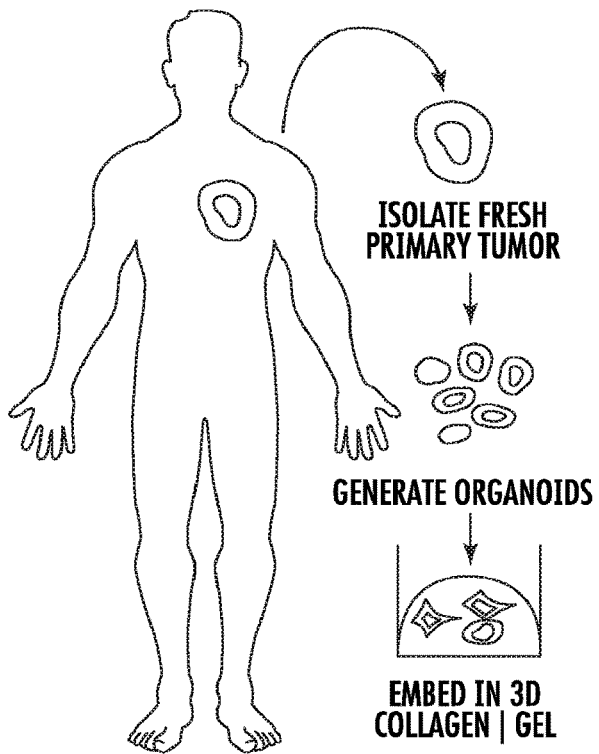
FIGS. 1A-1G depict (1A) Workflow for isolation of tumor organoids from fresh patient samples. (1B) Workflow of human tumor organoid generation with pictures taken during the experiment. (1C) Primary human tumor organoids were scored for invasive morphology into four categories. (1D) Invasive morphology was scored on viable patent samples (N=30 patient samples; N=1139 organoids) and sorted from the least to most invasion. (1E) Left panel: DIC image of a collectively invading strand of a tumor organoid into Collagen I. Right panel: Confocal image displaying the K14 expression in leader cells at the invasive front. (1F) Strong positive correlation between the level of invasion and K14 expression in the organoids. (1G) Strong positive correlation between the level of invasion and K14 conversion.
Figure 1B:
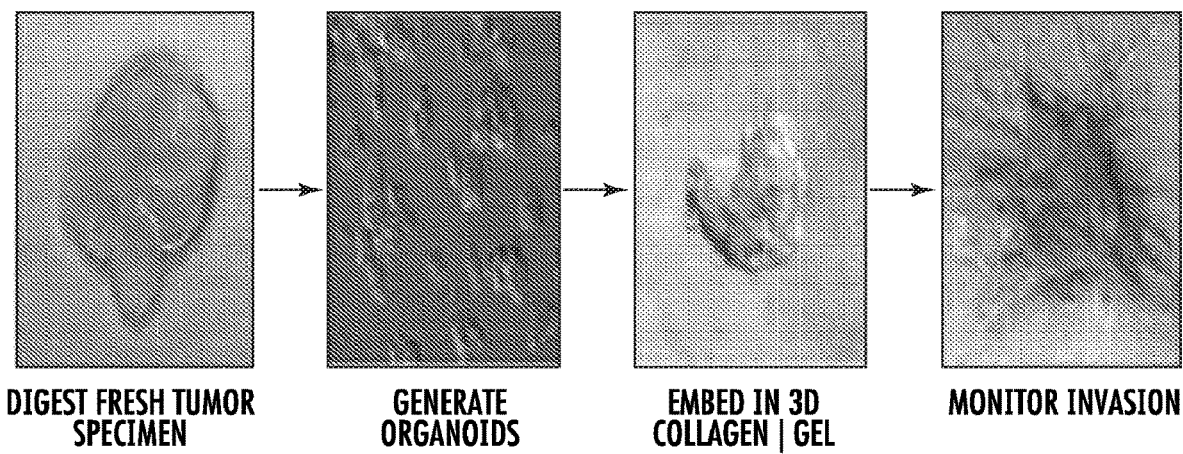
Figure 1C:
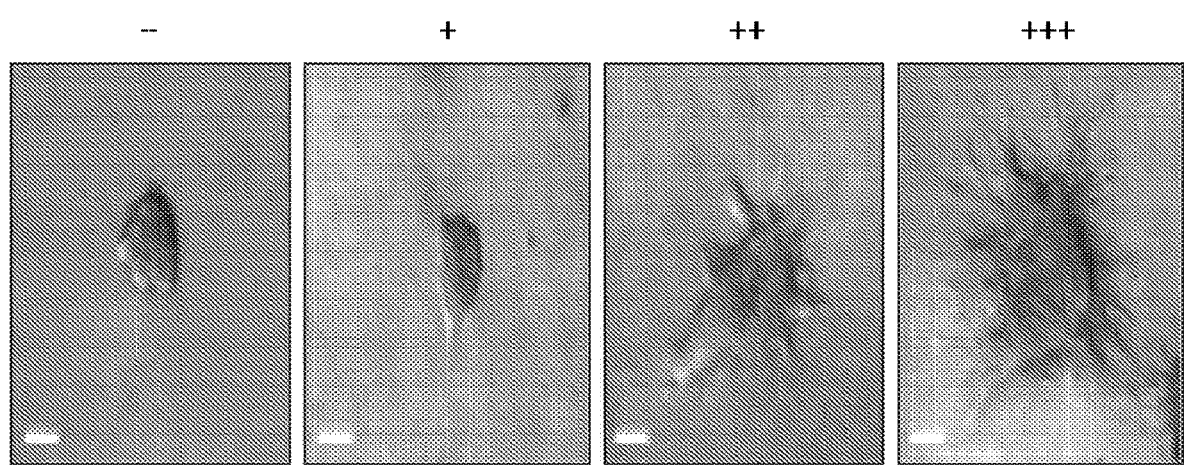
Figure 1D:
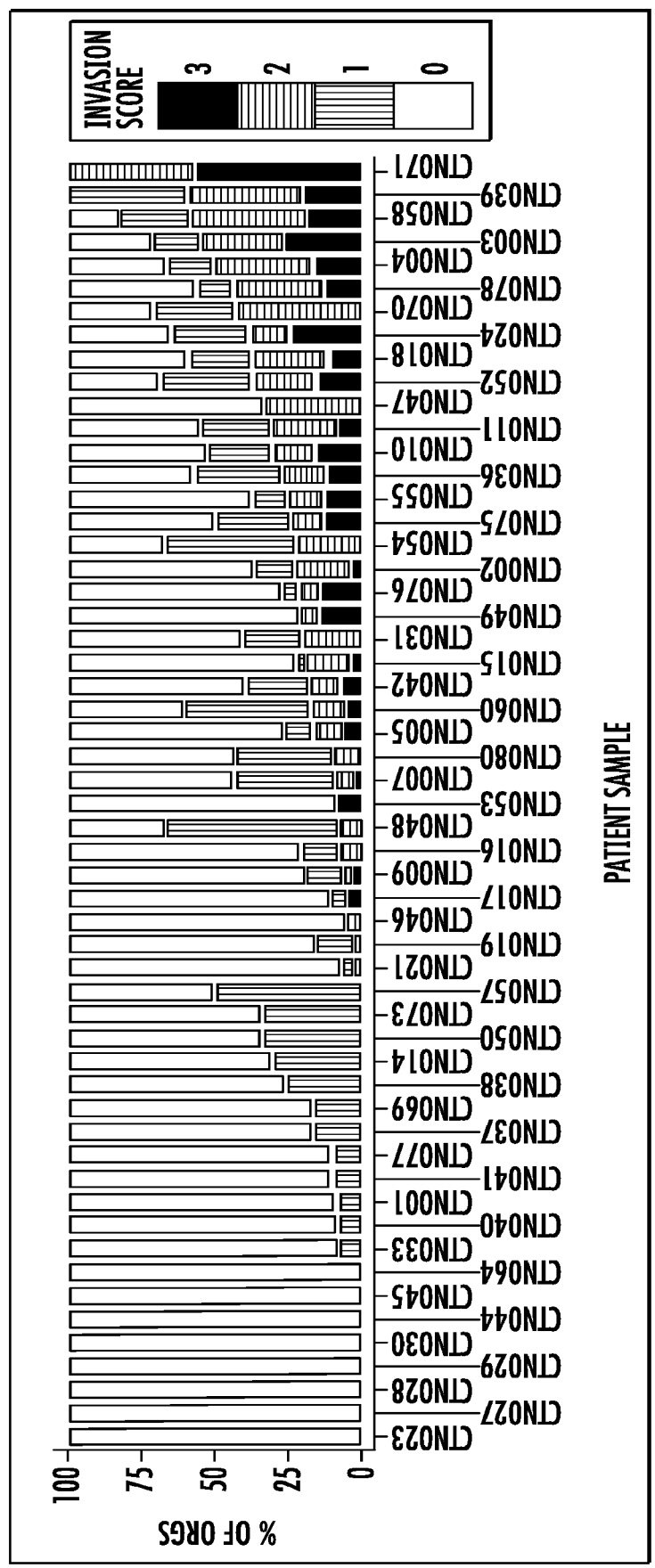
Figure 1E:
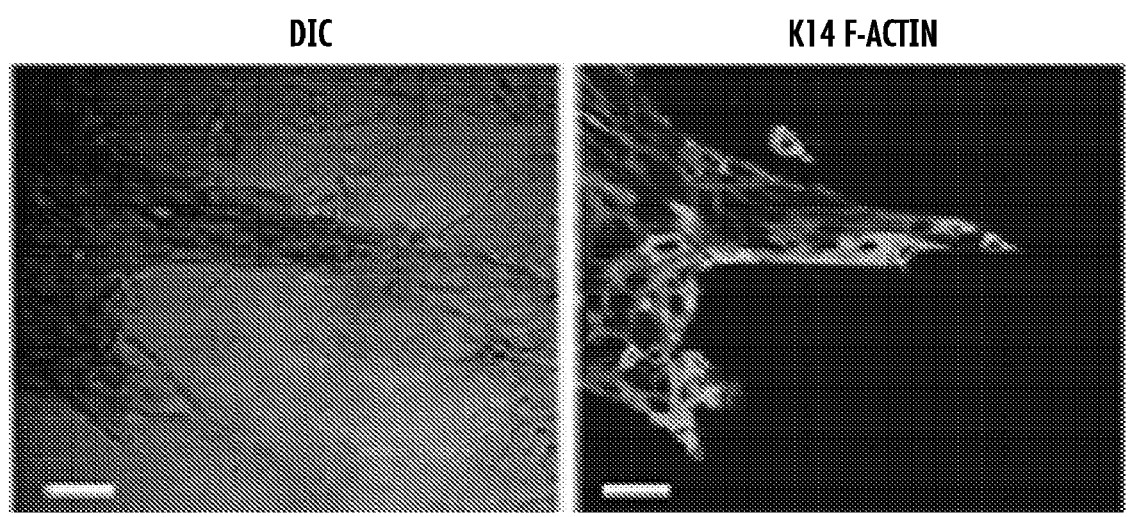
Figure 1F:
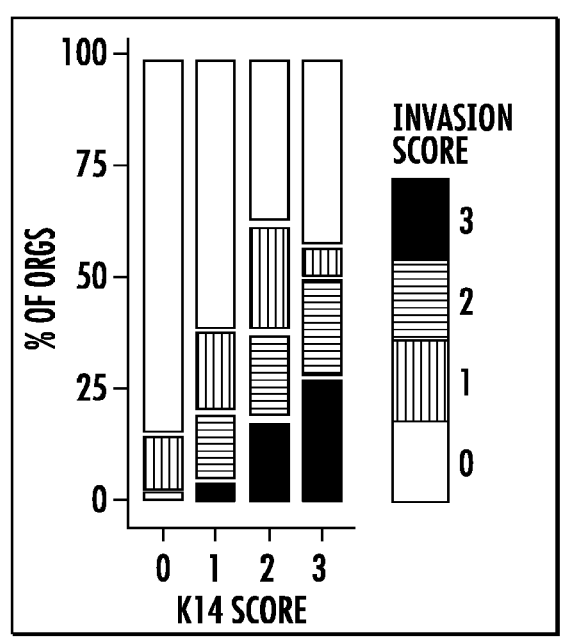
Figure 1G:
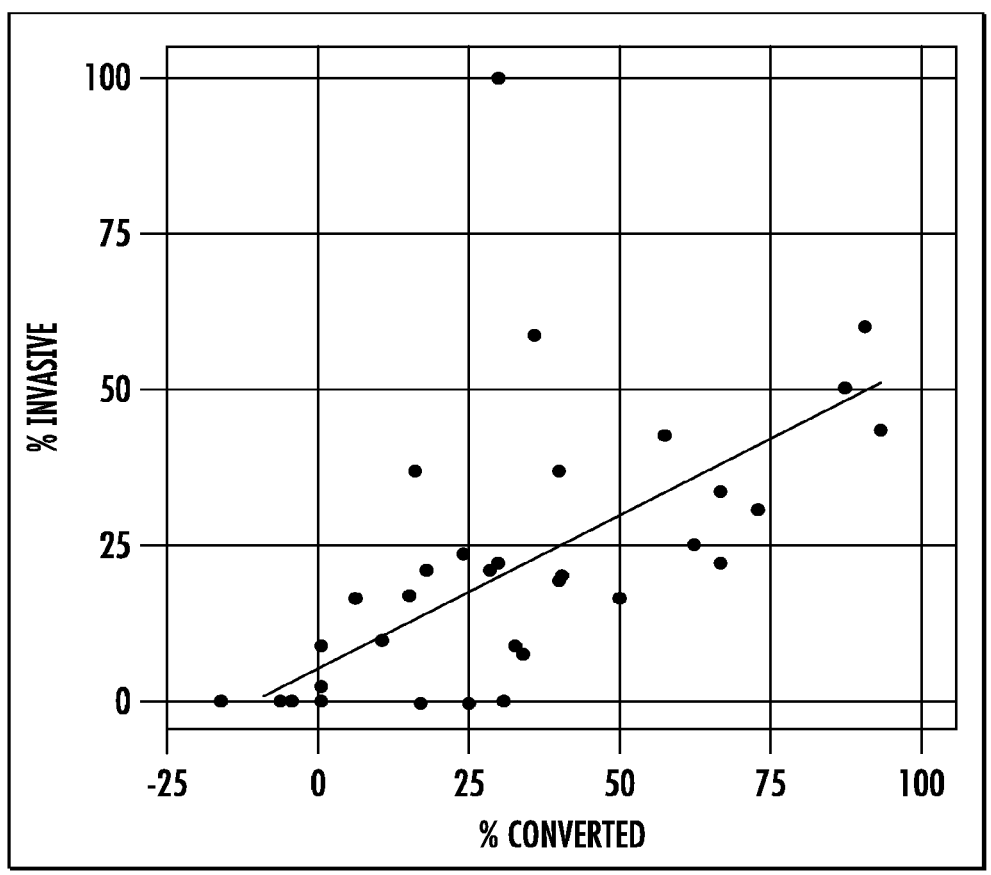

The present disclosure provides, among other things, compositions (e.g., autoantibodies) that inhibit the growth, viability, or mobility of (invasion by) a cancer cell. Also provided are applications, such as therapeutic and diagnostic methods, in which the agents are useful, as well as screening methods for identifying autoantibodies useful in the applications. While in no way intended to be limiting, exemplary compositions (e.g., pharmaceutical compositions and formulations), and methods for preparing and using these compositions are elaborated on below.

Applications

The disclosure features, e.g., methods for inhibiting the growth of a cancer cell, and/or treating a subject having a cancer, using one or more autoimmune antibodies. As used herein, the term "antibody" refers to whole antibodies including antibodies of different isotypes, such as IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody.

As used herein, the term "antibody fragment," "antigen-binding fragment," or similar terms refer to a fragment of an antibody that retains the ability to bind to an target antigen. Such fragments include, e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al. (2001) *J Immunol Methods* 248(1):47-66; Hudson and Kortt (1999) *J Immunol Methods* 231(1):177-189; Poljak (1994) *Structure* 2(12):1121-1123; Rondon and Marasco (1997) *Annual Review of Microbiology* 51:257-283, the disclosures of each of which are incorporated herein by reference in their entirety. Bispecific antibodies (including DVD-Ig antibodies; see below) are also embraced by the term "antibody." Bispecific antibodies are monoclonal, preferably human or humanized, antibodies that have binding specificities for at least two different antigens.

As used in herein, the term "antibody" also includes, e.g., single domain antibodies such as camelized single domain antibodies. See, e.g., Muyldermans et al. (2001) *Trends Biochem Sci* 26:230-235; Nuttall et al. (2000) *Curr Pharm Biotech* 1:253-263; Reichmann et al. (1999) *J Immunol Meth* 231:25-38; PCT application publication nos. WO 94/04678 and WO 94/25591; and U.S. Pat. No. 6,005,079, all of which are incorporated herein by reference in their entireties. In some embodiments, the disclosure provides single domain antibodies comprising two VH domains with modifications such that single domain antibodies are formed.

As used herein, the term "autoantibody" refers to refers to an antibody produced by the immune system that is directed against one or more of a host's own antigens, such as an epitope of a protein, a peptide, or a non-protein epitope. Such autoantibodies can be associated with autoimmune disease. Thus, in some embodiments, an autoimmune antibody is obtained from a subject (or the therapeutic antibody used (e.g., affinity matured antibody) is derived from an autoantibody from a subject) with an autoimmune disease. As used herein, the term "autoimmune disease" means a disease resulting from an immune response against a self-tissue or tissue component, including both self-antibody responses and cell-mediated responses. The term autoimmune disease, as used herein, encompasses organ-specific autoimmune diseases, in which an autoimmune response is directed against a single tissue, such as type I diabetes mellitus (T1D), Crohn's disease, ulcerative colitis, myasthenia gravis, vitiligo, Graves' disease, Hashimoto's disease, Addison's disease and autoimmune gastritis and autoimmune hepatitis. The term autoimmune disease also encompasses non-organ specific autoimmune diseases, in which an autoimmune response is directed against a component present in several or many organs throughout the body. Such autoimmune diseases include, for example, rheumatoid diseases, systemic lupus erythematosus, progressive systemic sclerosis and variants, polymyositis and dermatomyositis. Additional autoimmune diseases include pernicious anemia including some of autoimmune gastritis, primary biliary cirrhosis, autoimmune thrombocytopenia, Sjogren's syndrome, multiple sclerosis and psoriasis. Exemplary autoimmune diseases are elaborated on below.

Inflammatory myositis, which refers to the inflammation of muscle, is used to describe dermatomyositis, polymyositis, necrotizing myopathy, and inclusion-body myositis. Dermatomyositis affects 5 in every 100,000 persons in the United States (Furst et al., 2012). Common symptoms include a characteristic rash and muscle weakness which developed within a few weeks. The pathology of the disease includes binding of immune complexes to endothelial cells, activation of the complement system and subsequent lysis, leading to a decreased number of capillaries in the muscle (Mammen, 2010). Autoantibodies preferentially associated with dermatomyositis include those recognizing Mi-2, MDA5, TIF1γ, and NXP-2—each associated with a distinct phenotype (Shah et al., 2015).

Scleroderma is a systemic autoimmune disease best characterized by the hardening of the skin due to the increased synthesis of collagen leading to abnormal connective tissue (Fleming and Schwartz, 2008). The overall incidence rate of scleroderma in the adult population of the United States is approximately 20 per million per year (Mayes et al., 2003). Most patients affected by the disease present with Raynaud's phenomenon—reduced blood flow resulting in discoloration of fingers and toes. The most common scleroderma-specific autoantibodies include anticentromere, anti-topoisomerase, and anti-RNA polymerase (Shah et al., 2015).

Systemic lupus erythematosus (SLE) is a chronic and systemic autoimmune disease that affects joints, skin, lungs, kidneys, blood cells or heart and follows a relapsing and remitting course. The disease is characterized by a multisystem inflammation with the generation of autoantibodies including antinuclear, anti-ds DNA, anti-ribonucleoprotein, anti-Ro, and anti-La (Ippolito et al., 2011). The incidence of lupus is about 5-7 per 100,000 persons (Somers et al., 2014). Symptoms for the disease may vary between individuals, but usually include chest pain, fatigue, hair loss, mouth sores, fever with no cause, and/or a butterfly rash.

Methods for isolating B cell cells (e.g., B cells from a patient with an autoimmune disease) are known in the art. For example, the methods can involve obtaining a biological sample from a subject. A biological sample can be a biological fluid such as urine, whole blood or a fraction thereof (e.g., plasma or serum), saliva, semen, sputum, cerebrospinal fluid, tears, or mucus. A biological sample can be further fractionated, if desired, to a fraction containing particular analytes (e.g., proteins) of interest. For example, a whole blood sample can be fractionated into serum or into fractions containing particular types of proteins or cells. If desired, a biological sample can be a combination of different biological samples from a subject such as a combination of two different fluids.

Biological samples suitable for the invention may be fresh or frozen samples collected from a subject, or archival samples with known diagnosis, treatment and/or outcome history. The biological samples can be obtained from a subject, e.g., a subject having, suspected of having, or at risk of developing, an autoimmune disorder. Any suitable methods for obtaining the biological samples can be employed, although exemplary methods include, e.g., phlebotomy, swab (e.g., buccal swab), lavage, or fine needle aspirate biopsy procedure. Biological samples can also be obtained from bone marrow or spleen.

Methods for obtaining and/or storing samples that preserve the activity or integrity of cells in the biological sample are well known to those skilled in the art. For example, a biological sample can be further contacted with one or more additional agents such as appropriate buffers and/or inhibitors, including protease inhibitors, the agents meant to preserve or minimize changes (e.g., changes in osmolarity or pH) in protein structure. Such inhibitors include, for example, chelators such as ethylenediamine tetraacetic acid (EDTA), ethylene glycol tetraacetic acid (EGTA), protease inhibitors such as phenylmethylsulfonyl fluoride (PMSF), aprotinin, and leupeptin. Appropriate buffers and conditions for storing or otherwise manipulating whole cells are described in, e.g., Pollard and Walker (1997), "Basic Cell Culture Protocols," volume 75 of Methods in molecular biology, Humana Press; Masters (2000) "Animal cell culture: a practical approach," volume 232 of Practical approach series, Oxford University Press; and Jones (1996) "Human cell culture protocols," volume 2 of Methods in molecular medicine, Humana Press.

A sample also can be processed to eliminate or minimize the presence of interfering substances. For example, a biological sample can be fractionated or purified to remove one or more materials (e.g., cells) that are not of interest. Methods of fractionating or purifying a biological sample include, but are not limited to, flow cytometry, fluorescence activated cell sorting, and sedimentation.

In some embodiments, the antibody is present in a preparation made from blood from a subject. In some embodiments, the antibody is a recombinant antibody. Techniques for the preparation of recombinant antibody molecules are described in, e.g.: WO97/08320; U.S. Pat. Nos. 5,427,908; 5,508,717; Smith (1985) *Science* 225:1315-1317; Parmley and Smith (1988) *Gene* 73:305-318; De La Cruz et al. (1988) *J Biol Chem* 263:4318-4322; U.S. Pat. Nos. 5,403,484; 5,223,409; WO88/06630; WO92/15679; U.S. Pat. Nos. 5,780,279; 5,571,698; 6,040,136; Davis et al. (1999) *Cancer Metastasis Rev* 18(4):421-5; Taylor et al. (1992) *Nucleic Acids Res* 20: 6287-6295; and Tomizuka et al. (2000) *Proc Natl Acad Sci USA* 97(2): 722-727, the contents of each of which are incorporated herein by reference in their entirety.

The cell culture supernatants are screened for the desired antibodies, e.g., by immunofluorescent staining of target antigen-expressing cells, by immunoblotting, by an enzyme immunoassay, e.g. a sandwich assay or a dot-assay, or a radioimmunoassay.

For isolation of the antibodies, the immunoglobulins in the culture supernatants may be concentrated, e.g., by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with one or more surface polypeptides derived from a target antigen-expressing cell line, or with Protein-A or -G.

Another embodiment provides a process for the preparation of a bacterial cell line secreting antibodies directed against a target antigen in a suitable mammal. For example, a rabbit is immunized with pooled samples from target antigen-expressing tissue or cells or the target antigen itself (or fragments thereof). A phage display library produced from the immunized rabbit is constructed and panned for the desired antibodies in accordance with methods well known in the art (such as, e.g., the methods disclosed in the various references incorporated herein by reference).

A "subject," as used herein, can be any mammal. For example, a subject can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the subject is an infant (e.g., a human infant). The subject can have cancer, an autoimmune disease, or both a cancer and an autoimmune disease.

The compositions described herein can be formulated as a pharmaceutical solution, e.g., for administration to a subject treating a cancer. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see e.g., Berge et al. (1977) *J Pharm Sci* 66:1-19).

The compositions can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). In some embodiments, a composition can be formulated, for example, as a buffered solution at a suitable concentration and suitable for storage at 2-8° C. (e.g., 4° C.). In some embodiments, a composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions described herein are stable in storage for at least 1 year at 2-8° C. (e.g., 4° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing a composition intended for systemic or local delivery can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion (see below).

The compositions can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filtered sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

The compositions described herein can also be formulated in immunoliposome compositions. Such formulations can be prepared by methods known in the art such as, e.g., the methods described in Epstein et al. (1985) *Proc Natl Acad Sci USA* 82:3688; Hwang et al. (1980) *Proc Natl Acad Sci USA* 77:4030; and U.S. Pat. Nos. 4,485,045 and 4,544,545. Liposomes with enhanced circulation time are disclosed in, e.g., U.S. Pat. No. 5,013,556.

In certain embodiments, compositions can be formulated with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

In some embodiments, compositions described herein are administered in an aqueous solution by parenteral injection. The disclosure features pharmaceutical compositions comprising an effective amount of the agent (or more than one agent) and optionally include pharmaceutically acceptable diluents, preservatives, solubilizers, emulsifiers, adjuvants and/or carriers. Such compositions include sterile water, buffered saline (e.g., Tris-HCl, acetate, phosphate), pH and ionic strength; and optionally, additives such as detergents and solubilizing agents (e.g., TWEEN® 20, TWEEN 80, Polysorbate 80), anti-oxidants (e.g., ascorbic acid, sodium metabisulfite), and preservatives (e.g., thimersol, benzyl alcohol) and bulking substances (e.g., lactose, mannitol). The formulations may be sterilized, e.g., using filtration, incorporating sterilizing agents into the compositions, by irradiating the compositions, or by heating the compositions.

As described above, relatively high concentration compositions can be made. For example, the compositions can be formulated at a concentration of the active agent of between about 10 mg/mL to 100 mg/mL (e.g., between about 9 mg/mL and 90 mg/mL; between about 9 mg/mL and 50 mg/mL; between about 10 mg/mL and 50 mg/mL; between about 15 mg/mL and 50 mg/mL; between about 15 mg/mL and 110 mg/mL; between about 15 mg/mL and 100 mg/mL; between about 20 mg/mL and 100 mg/mL; between about 20 mg/mL and 80 mg/mL; between about 25 mg/mL and 100 mg/mL; between about 25 mg/mL and 85 mg/mL; between about 20 mg/mL and 50 mg/mL; between about 25 mg/mL and 50 mg/mL; between about 30 mg/mL and 100 mg/mL; between about 30 mg/mL and 50 mg/mL; between about 40 mg/mL and 100 mg/mL; between about 50 mg/mL and 100 mg/mL; or between about 20 mg/mL and 50 mg/mL). In some embodiments, compositions can be formulated at a concentration of greater than 5 mg/mL and less than 50 mg/mL. Methods for formulating a protein in an aqueous solution are known in the art and are described in, e.g., U.S. Pat. No. 7,390,786; McNally and Hastedt (2007), "Protein Formulation and Delivery," Second Edition, *Drugs and the Pharmaceutical Sciences*, Volume 175, CRC Press; and Banga (1995), "Therapeutic peptides and proteins: formulation, processing, and delivery systems," CRC Press. In some embodiments, the aqueous solution has a neutral pH, e.g., a pH between, e.g., 6.5 and 8 (e.g., between and inclusive of 7 and 8). In some embodiments, the aqueous solution has a pH of about 6.6, 6.7, 6.8, 6.9, 7, 7.1, 7.2, 7.3, 7.4, 7.5, 7.6, 7.7, 7.8, 7.9, or 8.0. In some embodiments, the aqueous solution has a pH of greater than (or equal to) 6 (e.g., greater than or equal to 6.1, 6.2, 6.3, 6.4, 6.5, 6.6, 6.7, 6.8, 6.9, 7, 7.1, 7.2, 7.3, 7.4, 7.5, 7.6, 7.7, 7.8, or 7.9), but less than pH 8.

Nucleic acids encoding a therapeutic polypeptide can be incorporated into a gene construct to be used as a part of a gene therapy protocol to deliver nucleic acids that can be used to express and produce agents within cells. Expression constructs of such components may be administered in any therapeutically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1 (HSV-1), or recombinant bacterial or eukaryotic plasmids. Viral vectors can transfect cells directly; plasmid DNA can be delivered with the help of, for example, cationic liposomes (lipofectin) or derivatized, polylysine conjugates, gramicidin S, artificial viral envelopes or other such intracellular carriers, as well as direct injection of the gene construct or $CaPO_4$ precipitation (see, e.g., WO04/060407) carried out in vivo. Examples of suitable retroviruses include pLJ, pZIP, pWE and pEM which are known to those skilled in the art (see, e.g., Eglitis et al. (1985) *Science* 230:1395-1398; Danos and Mulligan (1988) *Proc Natl Acad Sci USA* 85:6460-6464; Wilson et al. (1988) *Proc Natl Acad Sci USA* 85:3014-3018; Armentano et al. (1990) *Proc. Natl. Acad. Sci. USA* 87:6141-6145; Huber et al. (1991) *Proc Natl Acad Sci USA* 88:8039-8043; Ferry et al. (1991) *Proc Natl Acad Sci USA* 88:8377-8381; Chowdhury et al. (1991) *Science* 254:1802-1805; van Beusechem et al. (1992) *Proc Natl Acad Sci USA* 89:7640-7644; Kay et al. (1992) *Human Gene Therapy* 3:641-647; Dai et al. (1992) *Proc Natl Acad Sci USA* 89:10892-10895; Hwu et al. (1993) *J Immunol* 150:4104-4115; U.S. Pat. Nos. 4,868,116 and 4,980,286; PCT Publication Nos. WO89/07136, WO89/02468, WO89/05345, and WO92/07573). Another viral gene delivery system utilizes adenovirus-derived vectors (see, e.g., Berkner et al. (1988) *BioTechniques* 6:616; Rosenfeld et al. (1991) *Science* 252:431-434; and Rosenfeld et al. (1992) *Cell* 68:143-155). Suitable adenoviral vectors derived from the adenovirus strain Ad type 5 dl324 or other strains of adenovirus (e.g., Ad2, Ad3, Ad7, etc.) are known to those skilled in the art. Yet another viral vector system useful for delivery of the subject gene is the adeno-associated virus (AAV). See, e.g., Flotte et al. (1992) *Am J Respir Cell Mol Biol* 7:349-356; Samulski et al. (1989) *J Virol* 63:3822-3828; and McLaughlin et al. (1989) *J Virol* 62:1963-1973.

When compositions are to be used in combination with a second active agent, the compositions can be coformulated with the second agent or the compositions can be formulated separately from the second agent formulation. For example, the respective pharmaceutical compositions can be mixed, e.g., just prior to administration, and administered together or can be administered separately, e.g., at the same or different times (see below).

The compositions described herein can be administered to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection (IM).

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

As used herein the term "effective amount" or "therapeutically effective amount", in an in vivo setting, means a dosage sufficient to treat, inhibit, or alleviate one or more symptoms of the disorder being treated or to otherwise provide a desired pharmacologic and/or physiological effect. The precise dosage will vary according to a variety of factors such as subject-dependent variables (e.g., age, immune system health, etc.), the disease, and the treatment being effected.

Suitable human doses of any of the antibodies or fragments thereof described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

Toxicity and therapeutic efficacy of such compositions can be determined by known pharmaceutical procedures in cell cultures or experimental animals (e.g., animal models of cancer). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents that exhibits a high therapeutic index are preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such antibodies or antigen-binding fragments thereof lies generally within a range of circulating concentrations of the antibodies or fragments that include the $ED_{50}$ with little or no toxicity. The dosage may vary within this range depending upon the dosage form employed and the route of administration utilized. A therapeutically effective dose can be estimated initially from cell culture assays. A dose can be formulated in animal models to achieve a circulating plasma concentration range that includes the $IC_{50}$ (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration is desired, cell culture or animal modeling can be used to determine a dose required to achieve a therapeutically effective concentration within the local site.

In some embodiments of any of the methods described herein, an agent can be administered to a mammal in conjunction with one or more additional therapeutic agents (e.g., therapeutic agents for treating a cancer). Suitable additional anti-cancer therapies include, e.g., chemotherapeutic agents, ionizing radiation, immunotherapy agents, or hyperthermotherapy. Chemotherapeutic agents include, but are not limited to, aminoglutethimide, amsacrine, anastrozole, asparaginase, bcg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, taxol, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into groups, including, for example, the following: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristine, vinblastine, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); immunomodulatory agents (thalidomide and analogs thereof such as lenalidomide (Revlimid, CC-5013) and CC-4047 (Actimid)), cyclophosphamide; anti-angiogenic compounds (TNP-470, genistein) and growth factor inhibitors (vascular endothelial growth factor (VEGF)-inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisone, and prednisolone); growth factor signal transduction kinase inhibitors; mitochondrial dysfunction inducers and caspase activators; and chromatin disruptors.

The term "immunotherapeutic agent" can include any molecule, peptide, antibody or other agent which can stimulate a host immune system to generate an immune response to a tumor or cancer in the subject. Various immunotherapeutic agents are useful in the compositions are known in the art and include, e.g., PD-1 and/or PD-1L inhibitors, CD200 inhibitors, CTLA4 inhibitors, and the like. Exemplary PD-1/PD-L1 inhibitors (e.g., anti-PD-1 and/or anti-PD-L1 antibodies) are known in the art and described in, e.g., International Patent Application Publication Nos. WO 2010036959 and WO 2013/079174, as well as U.S. Pat. Nos. 8,552,154 and 7,521,051, the disclosures of each of which as they relate to the antibody descriptions are incorporated herein by reference in their entirety. Exemplary CD200 inhibitors are also known in the art and described in, e.g., International Patent Application Publication No. WO 2007084321. Suitable anti-CTLA4 antagonist agents are described in International Patent Application Publication Nos. WO 2001/014424 and WO 2004/035607; U.S. Patent Application Publication No. 2005/0201994; and European Patent No. EP 1212422. Additional CTLA-4 antibodies are described in U.S. Pat. Nos. 5,811,097, 5,855,887, 6,051,227, and 6,984,720. It is understood that the immunomodulatory agents can also be used in conjunction with a compound described herein for the treatment of an infection, such a viral, bacterial, or fungal infection, or any other condition in which an enhanced immune response to an antigen of interest would be therapeutically beneficial.

The following examples are intended to illustrate, not to limit, this disclosure.

EXAMPLES

Example 1. Materials and Methods

Purification of Autoantibodies from Human Serum

Blood was collected from healthy controls or patients with autoimmune diseases (dermatomyositis, lupus, or scleroderma). To avoid the dilution of serum samples, zebra spin desalting columns (89882; Life Technologies) were used to perform buffer exchange into sodium phosphate for the subsequent steps. For purifying the total IgG from the serum, the flow through was collected from running the sample through Melon gel IgG spin purification kits (45206; Life technologies). The IgG concentrations of the sample was then estimated by coomassie staining of samples that were electrophoresed on SDS-PAGE gels. For estimating the standard curve, rabbit IgG samples of 5, 10, 20, 40 and 80 µg were run on each of these gels. Purified IgGs were then stored at −80° C.

Isolating Human Tumor Organoids

Using mechanical disruption, enzyme digestion, and centrifugation we purified fragments of primary mammary tumors called tumor organoids. Human tumors arrive from the Cooperative Human Tissue Network (CHTN) in DMEM. The media washed out, tumors are then treated very briefly with 5 mL of fungizone solution: 10 ml Pen-Strep (P4333; Sigma), 10 ml Fungizone (15290-018; Life Technologies), and 500 ml DPBS (D8662; Sigma). Primary breast tumors from patients with metastatic disease were minced with a scalpel, and digested them for one hour at 37° C. in collagenase solution: (DMEM (10565-018; Gibco) with 2 mg/ml collagenase (C2139; Sigma-Aldrich), 5% FBS (F0926; Sigma-Aldrich), 5 µg/ml insulin (19278; Sigma-Aldrich), GlutaMAX (35050-079; Gibco) and Penicilin-Streptamycin (15140-122; Gibco)). The suspension was centrifuged at 1500 rpm to remove adipocytes, and the pellet was treated with 2 U/µL DNase (D4263; Sigma-Aldrich) to separate out organoids. Single cells were removed using four quick spins at 1500 rpm, and the solution was enriched for organoids. Organoids were embedded in collagen I gels at a density of 1-2 organoids/µl and plated as 100-µl suspensions in 24-well (662892; Greiner Bio-One) or 8-well (154534; Lab Tek) coverslip-bottomed plates over a 37° C. heating block. Gels were allowed to polymerize for 30 min at 37° C. and then cultured in human tumor mammary epithelial medium: 100 ml DMEM with 4500 mg/L glucose, sodium pyruvate, and sodium bicarbonate, without L-glutamine, liquid, sterile-filtered, suitable for cell culture (D6546 Sigma; 1 mL of 100× GlutaMAX (35050-061 Life Technologies); 100 U/ml/100 µg/ml Pen-Strep (1 ml of Pen 10,000 U/ml/Strep 10,000 µg/ml) (P4333 Sigma); 10 mM Hepes Buffer, pH 7.3 (1 ml of 1M stock) (118-089-721 Quality Biological, INC.); 0.075% BSA (250 ul of 30% stock) (A9576 Sigma); 10 ng/ml Cholera Toxin (1 ul of 1 mg/ml stock) (C8052 Sigma); 0.47 µg/ml Hydrocortisone (1 ml of 50 µg/ml stock in PBS) (H0396 Sigma); 5 µg/ml Insulin solution, human (125 µl of 4 mg/ml stock or 504 of 10 mg/mL stock) (19278 Sigma); 5 ng/ml EGF (5 µl of 100 µg/ml stock) (E9644 Sigma) for six days.

Preparation of Collagen Gels for Culturing Tumor Organoids

Tumor organoids isolated from primary human breast tumors were embedded in collagen solution prepared from rat tail collagen I (354236; Corning) using the following recipe. Combine 375 µL of 10×DMEM (D2429; Sigma) and 1004 of NaOH (S2770; Sigma) and mix well until the solution turns to a dark pink color. Add 3.5 mL of collagen I and mix well until the color remains stable. As the pH changes from acidic to neutral to basic, the solution changes color from yellow to light pink/orange to dark pink. Titrate with small volumes of NaOH until the desired color of light pink or salmon is attained. All steps were performed on ice. Allow this solution to polymerize on ice for 1-2 hours until the solution turns cloudy.

Culturing Human Tumor Organoids with Serum Autoantibodies

Tumor organoids collected on day 0 (day of plating them in culture) were fixed in 4% paraformaldehyde solution for 15 minutes. The remaining organoids were allowed to grow in culture medium with or without 10% of a specific autoantibody* (2254 of culture medium plus 25 µL of autoantibody) for 6 days, or until the organoids were invasive into the surrounding collagen I gels. These gels were then fixed in 4% paraformaldehyde solution for 15 minutes and analyzed for their levels of invasion.

(*—variations of this experiment were also performed at 4% culture volume, and at a constant autoantibody concentration of 150 ug/mL or 1 uM.)

Immunofluorescence

Tumors organoids in collagen I gels were harvested at day 6 of culture and fixed for 15 minutes in 4% paraformaldehyde. They were then embedded in Tissue Tek® Optimal Cutting Temperature compound (O.C.T., Sakura) and frozen at −80° C. overnight. O.C.T blocks were sectioned at 50 micron thickness using a Leica cryostat (Leica Biosystems, Germany) set to −27° C. For antibody staining, the O.C.T was removed by rinsing with PBS for 45 minutes. Samples were blocked for 2 hours with 10% FBS/1% BSA/PBS solution, incubated with the serum autoantibodies (50 ug/ml) diluted in a 1% FBS/1% BSA/PBS solution overnight at 4° C. Samples were rinsed with PBS for 30 minutes.

Slides were incubated with goat anti-human 488 secondary antibody (A-11013; Life Technologies) diluted at a 1:200 ratio in a 1% FBS/1% BSA/PBS solution for three hours. Samples were rinsed with PBS for 30 minutes, mounted with Fluoromount (F4680; Sigma), and sealed with coverslips.

DIC Microscopy

Differential interference contrast (DIC) imaging of tumor organoids was conducted using an LD Plan-Neofluar 20×/0.4 Korr Ph2 objective lens and a Cell Observer System with a Zeiss AxioObserver Z1 and a AxioCam MRM camera (Carl Zeiss, Germany). Photoshop CS6 and ImageJ were used as needed to adjust levels and gamma for each channel on entire images to maximize image clarity.

Confocal Microscopy

Confocal imaging of fixed tumor sections was conducted with a Zeiss 780 laser scanning confocal microscope (Carl Zeiss, Germany). A 40×LD LCI C-Apochromat objective lens (Carl Zeiss) was used for high magnification image acquisition with water used as the imaging medium. Acquisition of fixed images was performed using Zen 2011.

Scoring Criteria for Invasion and K14 Intensity

Invasion Scoring: Score b: The organoid cannot be evaluated or not an organoid. Score d: The organoid contains only cells that are rounded up. If there are small clusters, the organoid is not dead. Score 0: Organoid has rounded borders. Score 1: Organoid has at least one protrusive cell or a wide front with no clear leaders or has an invasive strand but the tip is out of focus. Score 2: Organoid has two or fewer invasive strands (defined as containing at least 4 cells in the strand, even if the tip of the strand is blunt). Score 3: Organoid has three or more large invasive strands.

K14 intensity scoring: Score 0: Organoid is negative for K14. Score 1: Organoid has a weak diffuse staining or less than 5% focal K14 positive cells. Score 2: Organoid has bright diffused staining or greater than 50% of its surface that is K14 positive. Score 3: Organoid has greater than 75% surface with K14 positive cells where individual cells are clearly identified.

Example 2. Results

An Ex-Vivo 3D Culture System for Monitoring Invasion of Human Tumor Organoids Breast cancers use several mechanisms to invade into surrounding tissues, yet our understanding of the spectrum of invasive behaviors in human breast tumors is limited. Based on a 3D organoid assay previously developed (Cheung et al., 2013), K14 positive leader cells participating in the process of collective invasion in tumors from mice models of metastatic breast cancer were identified. A protocol was optimized for isolating tumor organoids from typically 0.2 g of tumor sample obtained at the time of patient surgery (FIG. 1, panel A and B).

70 human breast tumors (received from the Cooperative Human Tissue Network) were processed, and organoids from 57 of these tumor samples (81% success rate) were retrieved. The protocol was optimized to isolate a median of 1333 organoids per gram of tissue received. These tumor organoids were then embedded in collagen I gels to allow us to quantify their invasive behavior and to define the molecular phenotype of leader cells. When embedded in a collagen matrix, tumor organoids invade and extend several multicellular invasive strands (FIG. 1, Panel C) (Nguyen-Ngoc et al., 2012). The leader cells of such invasive strands are positive for K14, a basal epithelial marker (Cheung et al., 2013).

In this cohort of 70 tumors, only ~30% of tumors invaded efficiently into fibrillar collagen, while the others failed to invade despite robust growth in culture (FIG. 1, Panel D). Consistent with data from murine tumors, the cells leading the invasion front were K14+ for more than 95% of leaders identified (FIG. 1, Panel E). The level of invasion for 1981 organoids from 58 patient samples were scored on a scale of 0, 1, 2, or 3 (FIG. 1, Panel C). Similarly, 1505 organoids isolated from 56 patient samples for K14 expression intensity were also scored on a scale of 0, 1, 2 or 3. It was observed that the invasion efficiency of an organoid was strongly correlated with both the level of K14 expression (FIG. 1, Panel F; n=911 organoids, 53 tumors, p value<$2.2 \times 10^{-16}$) and induction of K14 expression in tumor cells (FIG. 1, Panel G; n=45 patient samples, R-correlation=0.795, p value=$6.52 \times 10^{-11}$).

Apart from these tumor samples, 11 normal mammary specimens were obtained from breast reduction surgeries. The tissue was processed in a manner similar to the tumors, and we were successful in isolating organoids from 73% of these samples. The mean isolation rate for normal mammary was 216 organoids per gram of tissue.

Serum Autoantibodies Show Specificity for Mammary Tumor Antigens

Purified IgGs from the sera of patients with lupus erythematosus, myositis, and scleroderma were obtained. Organoids generated from human breast tumors were fixed on day 6 of culture, and stained with eighteen autoantibodies. As a control, tumor tissue was stained with antisera collected from two normal patients (FIG. 2, Panel A).

Figures 2A, 2B:
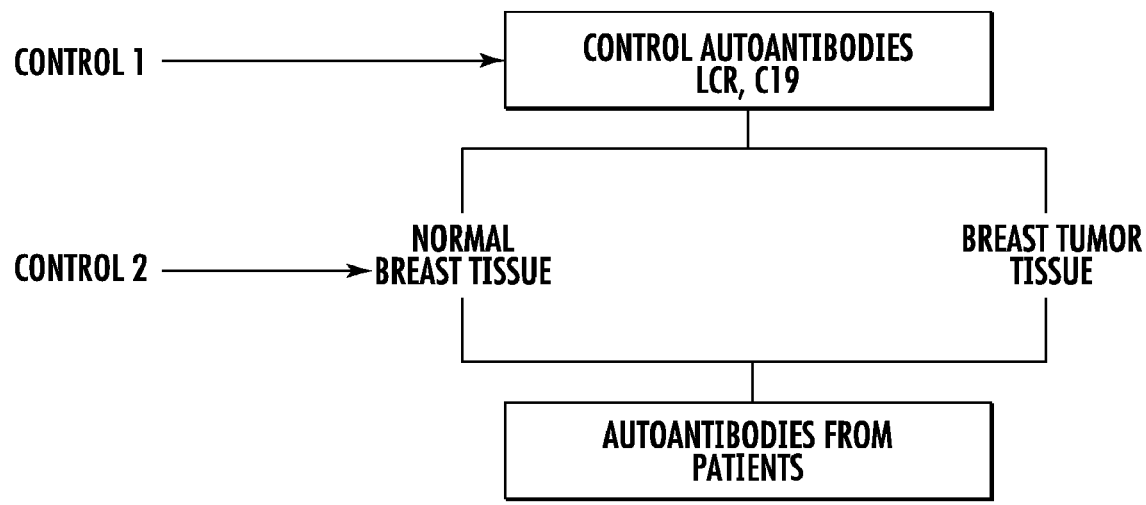

Positive staining was observed on ten of the eighteen autoantibodies (56%) tested against tumor tissue (FIG. 2, Panels B and C). Of these, 100% (10/10) of the autoantibodies stained the cytoplasm of tumor cells and 50% (5/10) exhibited positive nuclear staining (FIG. 2, Panel C). Among the different diseases, 75%, 60% and 44% of the dermatomyositis, lupus and scleroderma antisera stained tumor organoids (FIG. 2, Panel B). In order to test if the autoantibodies specifically bind only to tumor antigens, these results were compared with those obtained by staining organoids generated from normal mammary reduction tissue. In this case, staining was observed with seventeen of these autoantibodies (95%). It was surprising to detect binding of patient derived autoantibodies on normal mammary. 94.1% (16/17) of antisera which showed positive staining stained the cytoplasm and 47.1% (8/17) stained the nucleus (FIG. 2, Panel C). Interestingly, while control antisera failed to stain the tumor tissue, they stained the normal mammary tissue.

Figure 3A:
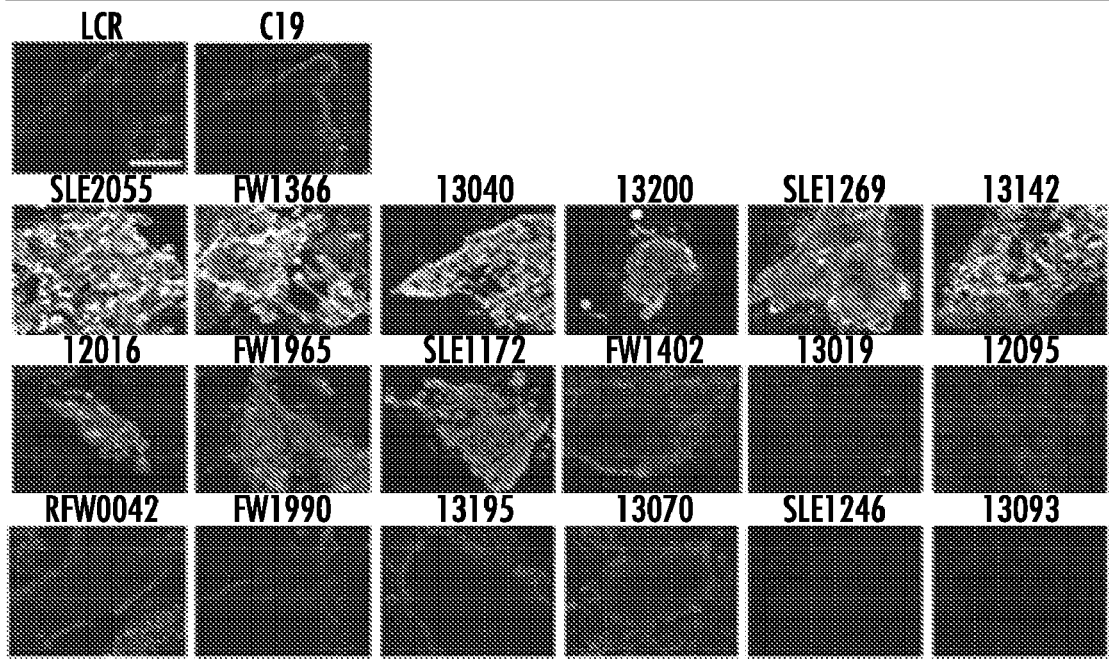
FIGS. 3A-3B. (3A) Representative images of staining results for two control antisera (C19, LCR) and eighteen patient antisera used to stain patient breast tumor organoids. Images are arranged in decreasing order of intensity. (3B) Representative images of staining results for two control antisera (C19, LCR) and eighteen patient antisera used to stain normal breast organoids. Images are order matched to the panel above.
Figure 3B:
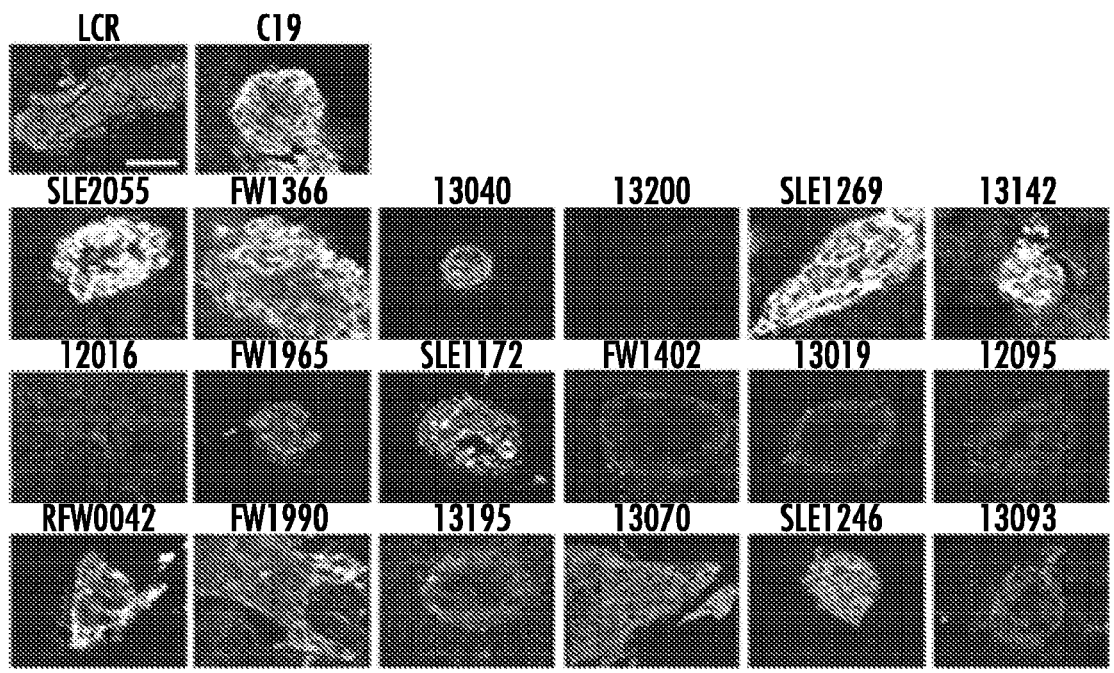

The presence and intensity of staining was also scored as − or +, and + or ++ respectively (FIG. 2, Panel C). Either cytoplasmic, nuclear or both cytoplasmic and nuclear staining was observed with each antiserum (FIG. 3, Panel A and B). While six antisera stained the normal and tumor tissues with equal intensities, ten stain normal tissue better. Two other antisera (13200 and 12106) showed a stronger binding to tumor organoids relative to those obtained from normal tissues (FIG. 3, Panel A and B). This represents an interesting circumstance wherein the antibody could be binding to antigens expressed specifically by tumor cells.

Figure 4:
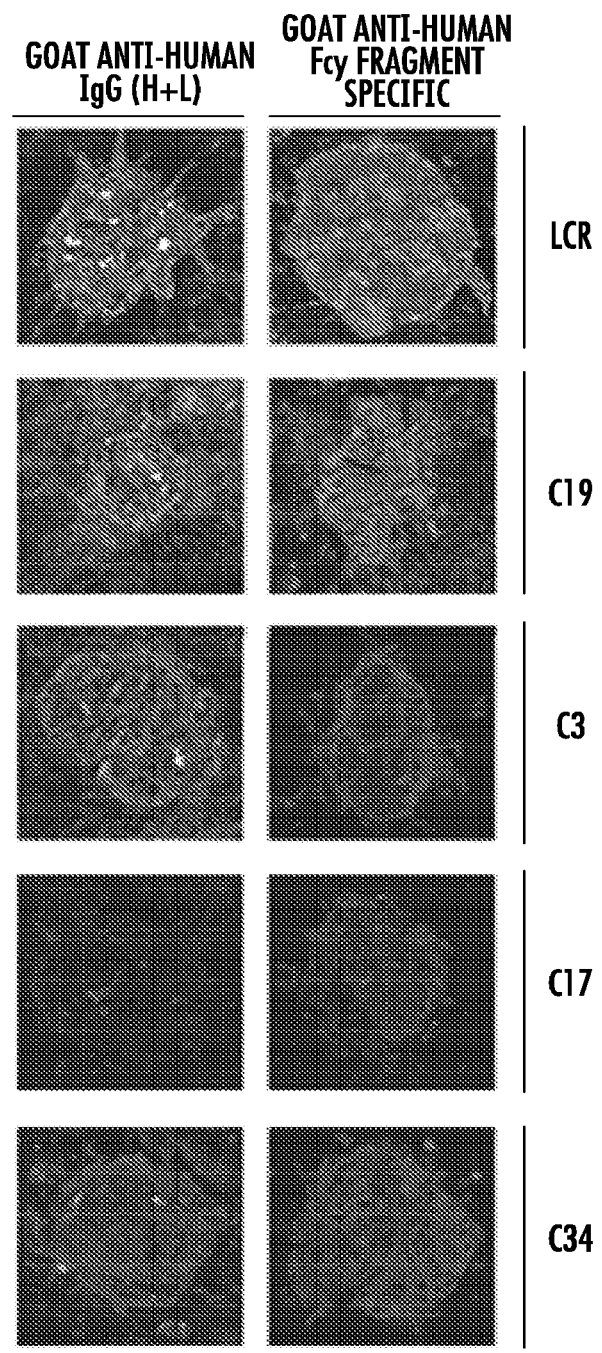
FIG. 4 depicts representative images of normal mammary organoids stained with control autoantibodies (LCR, C19, C3, C17 and C34). Staining procedures were completed with one of two secondary antibodies—goat anti-human IgG (H+L) or goat anti-human Fc-gamma specific IgG.

Given the increased binding of autoantibodies to normal tissue, a series of experiments were performed to detect immunoglobulin subtypes other than IgG. A secondary antibody specific to the Fc receptor of IgG was used, and the ability of five control autoantibodies (isolated from healthy individuals) to bind organoids derived from a single normal mammary reduction tissue was tested. Interestingly, binding patterns of autoantibodies did not alter significantly between IgG specific and non-specific secondary antibodies, suggesting that the detected signal was from IgGs (FIG. 4).

Figure 5:
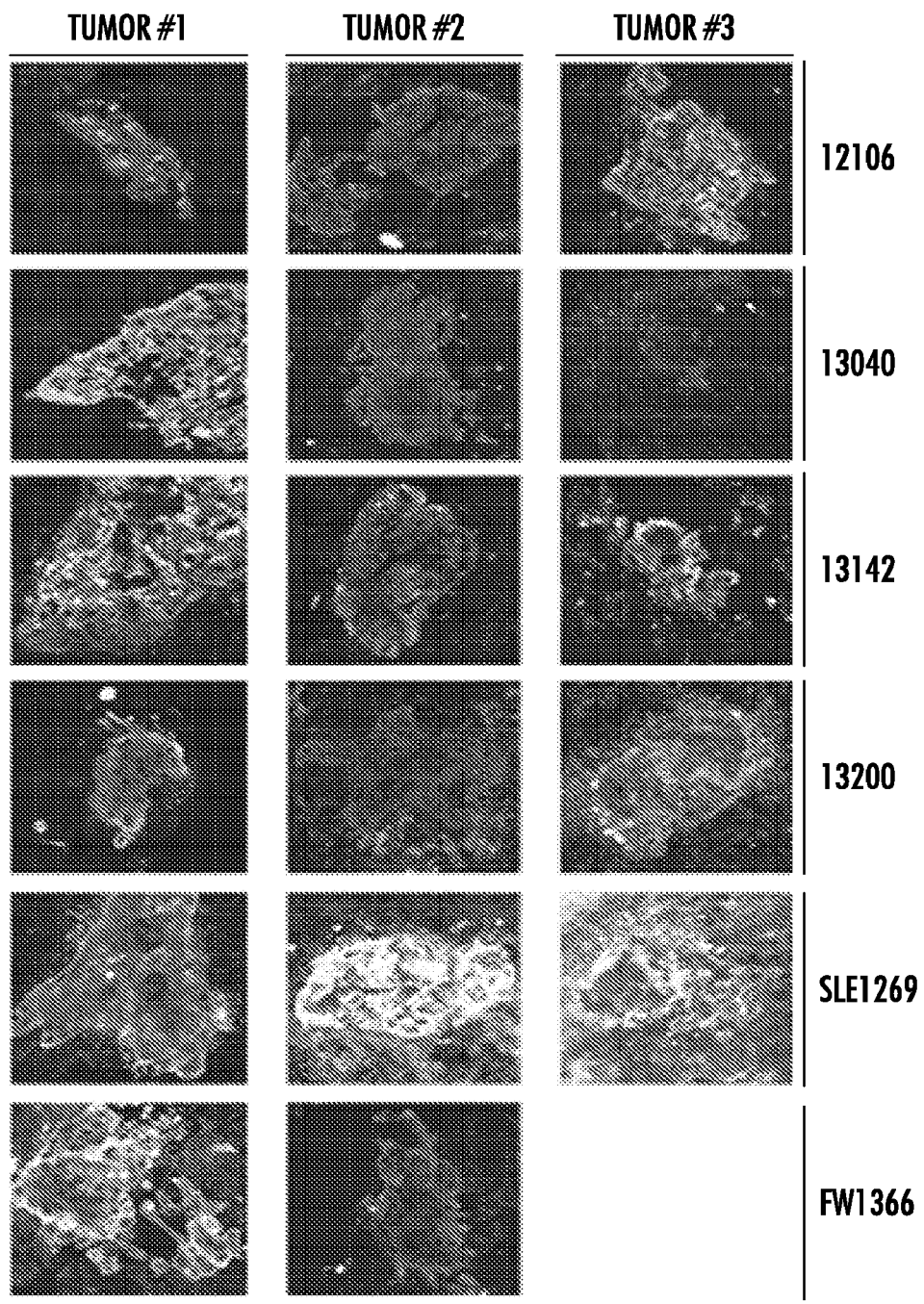
FIG. 5 depicts representative images of tumor organoids generated from three human breast tumors stained with patient derived autoantibodies (12106, 13040, 13142, 13200, S£1269, and FW1366).

Six autoantibodies (12106, 13040, 13142, 13200, SLE1269, and FW1366) among the panel of eighteen patient-derived autoantibodies showed significant binding against tumor antigens. The reproducibility of the staining pattern of these autoantibodies was tested against organoids generated from two other human mammary tumors. Tumor #1 was an ER+/PR+/HER2− with an invasive ductal histology, tumor #2 was a triple negative lobular carcinoma, and tumor #3 was an ER+/PR+/HER2− tumor with both invasive ductal and lobular characteristics. The staining pattern of the six autoantibodies varied significantly between each of these tumors. The differences were both in terms of signal intensity and localization (nuclear vs cytoplasmic or both) (FIG. 5).

To further assess the ability of autoantibodies to regulate tumor growth, purified IgG was obtained from patients with autoimmune disease and a known cancer status. These IgGs were also paired for identical known autoantibodies to allow for easier comparison.

Figure 6:
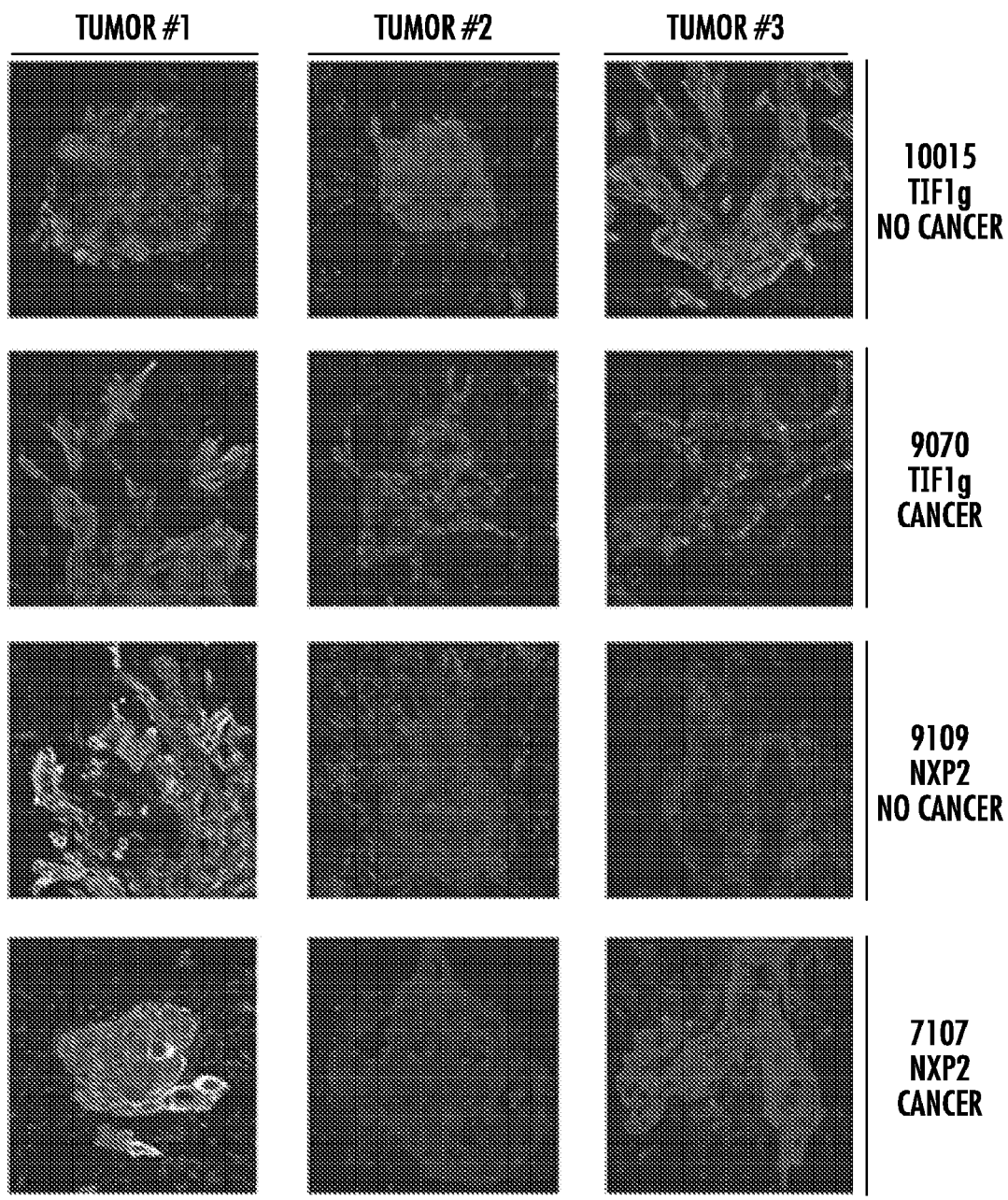
FIG. 6 depicts representative images of tumor organoids generated from three human breast tumors stained with patient derived autoantibodies. 10095 and 9070 are autoantibodies directed against TIF1 gamma purified from the serum of patients without or with cancer respectively. Similarly, anti-NXP2 autoantibodies 9109 and 7107 were purified from the serum of patients without or with cancer respectively.
Figure 7A:
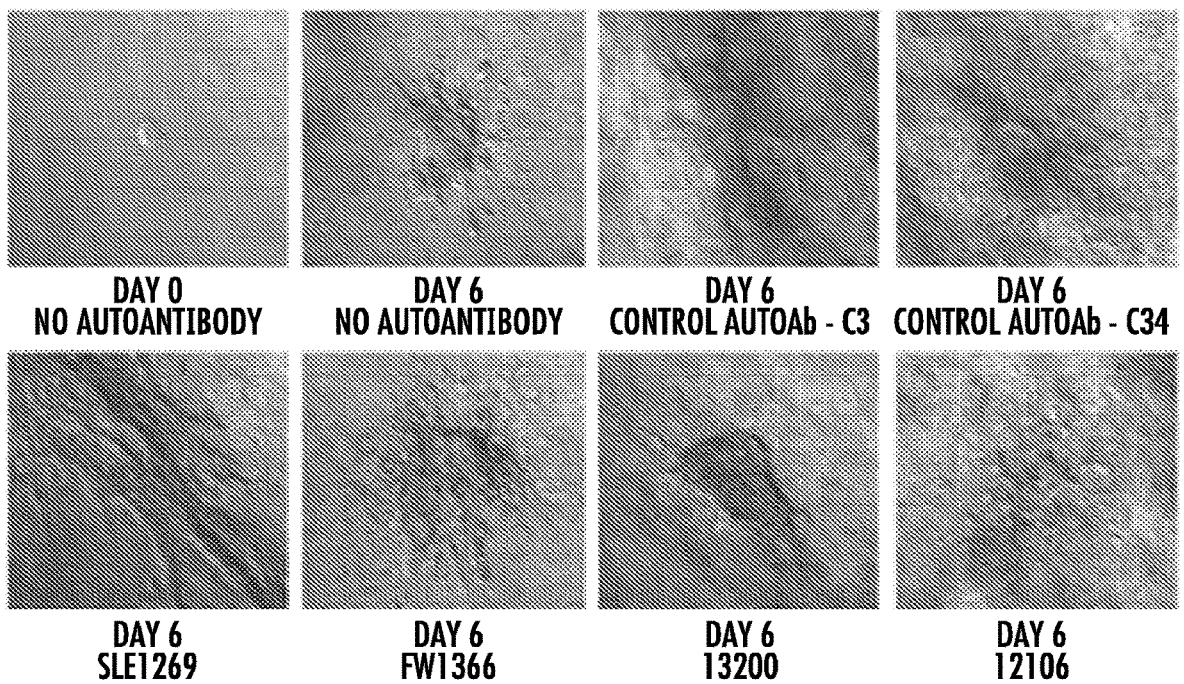
FIGS. 7A-7E. (7A) Effect of autoantibodies on tumor invasion in 3D organotypic culture. Representative DIC images depicting the invasion profile of tumor organoids collected on d0, or d6 without any autoantibody, or d6 with one of the following autoantibodies—SLE1269, FW1366, 13200, 12106, C33 or C34 (control autoantibodies). (7B) Bar graph comparing the cytotoxicity of each autoantibody. (7C) Table summarizing the cytotoxicity, percentage invasion and percentage decrease in invasion for each autoantibody (n=2 tumors). (7D) Bar graph comparing the effect of each autoantibody on collective invasion of tumor organoids derived from 2 tumors. (7E) Dose-dependency of autoantibodies 13200 and 12106 in reducing tumor invasion.
Figure 7B:
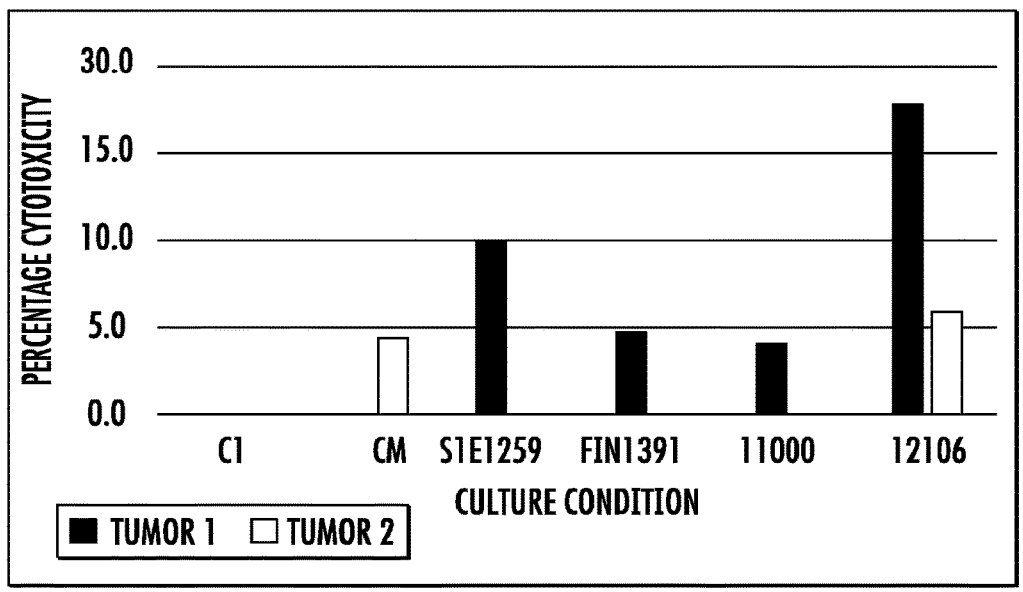
Figures 7C, 7D:
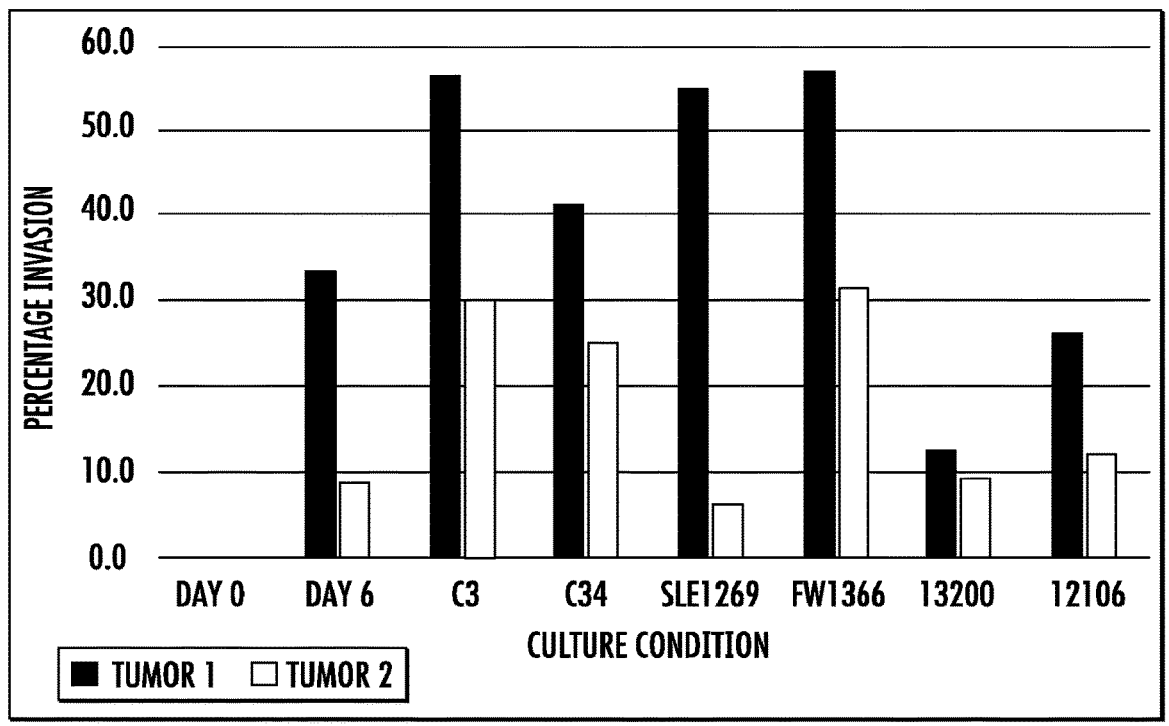
Figure 7E:
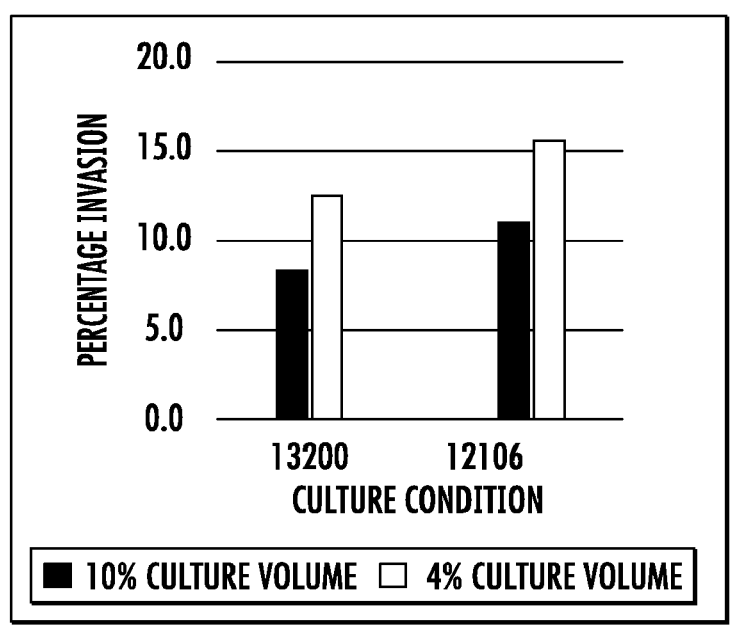

10015 and 9070 contained anti-TIF1 gamma antibodies, the former had no cancer, while the latter developed cancer. Similarly, 9109 and 7107 were anti-NXP2 antibody sera from individuals who had no cancer and cancer respectively. The ability of these autoantibodies to bind organoids generated from three human breast tumors—two ER+/PR+/HER2− tumors and one triple negative (ER−/PR−/HER2−) tumor—was tested. One anti-TIF1g autoantibody from a patient with cancer (9070), stained the nucleus, while an autoantibody from a no cancer patient (10015) did not show nuclear staining (2/3 tumors) (FIG. 6).

Serum Autoantibodies Regulate Tumor Invasion Inrganotypic Cultures

A series of experiments were performed to determine if autoantibodies derived from patient sera could affect tumor progression in a 3D organotypic culture system. Organoids derived from human tumors were cultured with autoantibodies. Four autoantibodies were selected that gave interesting staining patterns with previous experiments—SLE1269, FW1366, 13200, and 12106. Each autoantibody was added at a concentration of 10% of the total culture volume. A dying organoid loses its smooth borders and individual cells start rounding up. Based on this change in morphology, cytotoxicity of each autoantibody was assessed. The control antibodies showed no cytotoxicity, while patient-derived antibodies caused minimal (4-17%) cell death (FIG. 7, Panel B and C).

The effect of serum autoantibodies on tumor invasion was also assessed. The tumor organoids generated from two primary breast tumors (both ER+/PR+/HER2−) were not invasive on day 0 (or the day of plating organoids in culture), but became invasive at day 6 of culture (FIG. 7, Panel A). The baseline level of invasion of the two tumors in the absence of autoantibodies was 33.3% (9/27 of the organoids analyzed) and 8.3% (2/24 of the organoids analyzed), respectively (FIG. 7, Panel C). Interestingly, in the presence of antibodies isolated from no disease controls (C3 and C34), invasion of organoids increased to 56.3% and 41.2% respectively for tumor #1 and 30% and 25% respectively for tumor #2 (FIG. 7, Panels A and C). The patient-derived autoantibodies FW1366 increased tumor invasion to 57.1% for tumor #1 and 31.6% for tumor #2 (FIG. 7, Panels A, C, and D). Autoantibodies 13200 and 12106, on the other hand, decreased invasion in both tumors to 12.5% and 26.1% respectively for tumor #1 and 8.7% and 7.8% respectively for tumor #2 (FIG. 7, Panels A, C, and D). When compared to the no-antibody control, 13200 decreased tumor invasion by 77.8% (tumor #1) and 70.1% (tumor #2). Similarly, 12106 decreased invasion by 53.6% and 60.8% in tumors #1 and #2 respectively. Interestingly, both 13200 and 12106 were the autoantibodies that stained tumor organoids better than normal organoids. Purified IgG SLE1269 increased baseline invasion of tumor #1 to 55%, but decreased the baseline invasion of tumor #2 to 5.9% (FIG. 7, Panel A, C, and D).

The ability of autoantibodies to block invasion was dose dependent. Organoids isolated from tumor #2 were cultured with a lower dosage (4% culture volume) of 13200 and 12106. The functional effects of the autoantibodies 13200 and 12106 were dose dependent, with the lower dosages decreasing invasion by 56.5% and 44.4% respectively (FIG. 7, Panel E). However, even this lower dose was sufficient to reduce tumor invasion compared to control autoantibodies.

Autoantibodies from No Cancer Patients Reduce Tumor Invasion More Effectively Than Their Cancer Counterparts A series of experiments were performed to determine the effect of serum autoantibodies on tumor invasion was dependent on the cancer status of the patient. Since the cancer statuses of patients from whom the previous set of autoantibodies were collected was unknown, purified IgGs 10015 (anti-TIF1g, no cancer), 9070 (anti-TIF1g, cancer), 7107 (anti-NXP2, no cancer), and 9109 (anti-NXP2, cancer) were used.

Figure 8C:
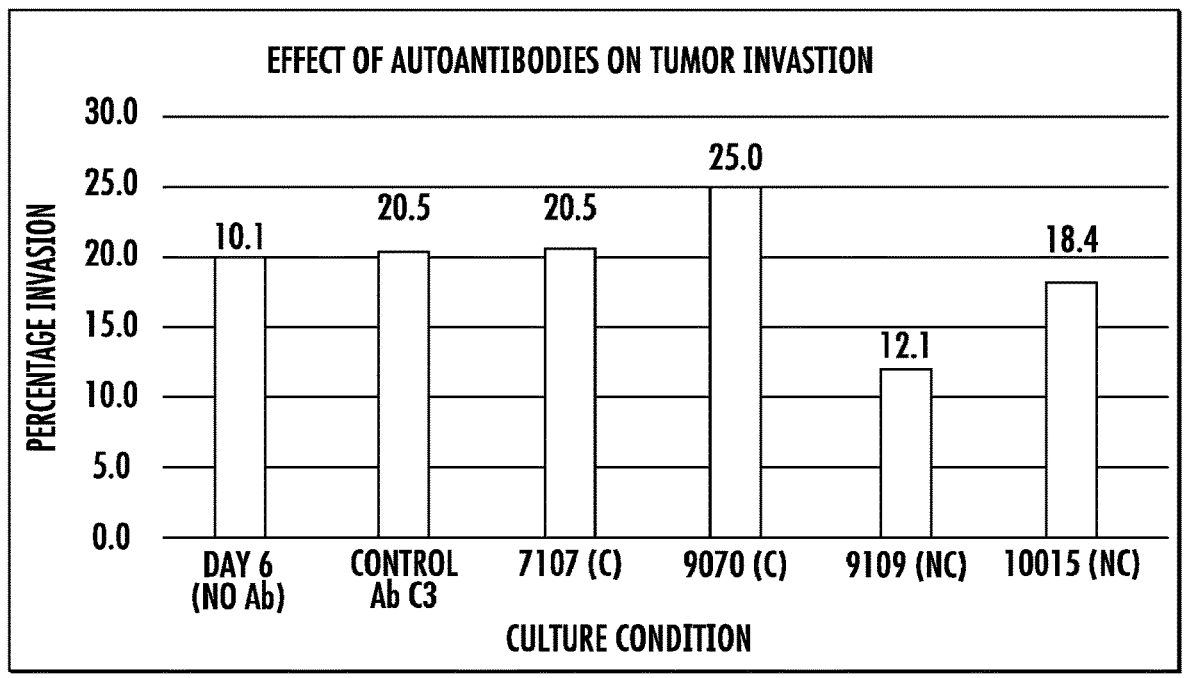
Figure 8D:
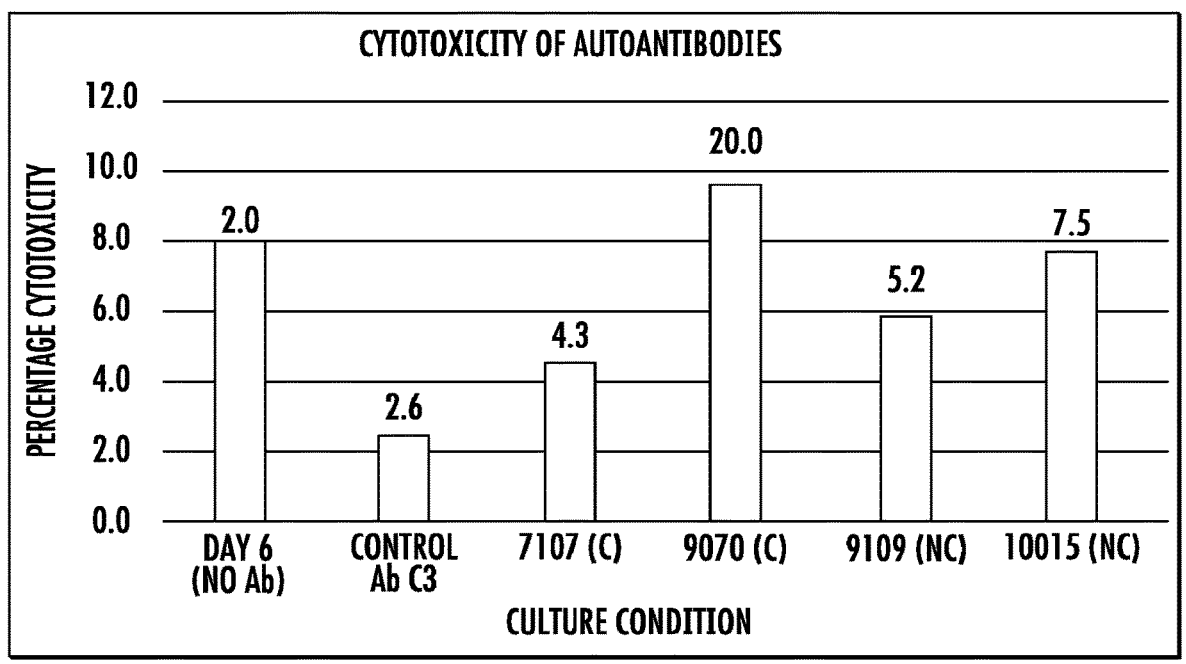
Figure 9:
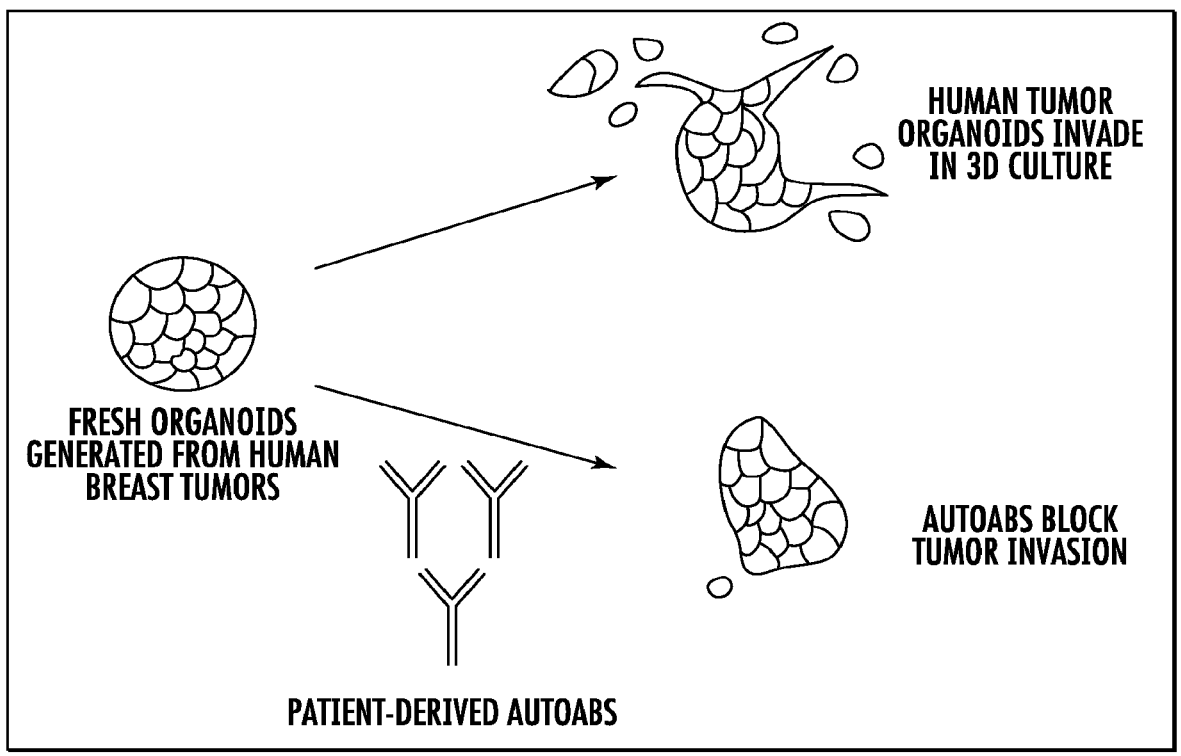
FIG. 9 depicts a working model: autoantibodies derived from patients with autoimmune diseases (AutoAbs) block tumor invasion in 3D organotypic cultures.

The tumor (#3) used for this set of experiments was a ER+/PR+/HER2− breast tumor whose organoids were 20% invasive in the absence of any autoantibodies (FIG. 8, Panel B). When cultured with 150 µg/mL of control antibody C34, the invasion levels remained almost unchanged at 20.5% (FIG. 8, Panels B and C). However, patient derived autoantibodies added at the same concentration altered tumor invasion in 3D culture. Antibodies derived from patients with cancer—7107 (anti-NXP2) and 9070 (anti TIF1g)—increased tumor invasion to 20.9% and 25% respectively. On the other hand, IgGs isolated from autoimmune patients with no cancer—9109 (anti-NXP2) and 10015 (anti TIF1g)—decreased tumor invasion to 12.1% and 18.4% respectively. All of the above autoantibodies had minimal cytotoxicity, ranging from 2-10% (FIG. 8, Panel B and C).

In conclusion, autoantibodies isolated from patients with no cancer are more effective in reducing tumor invasion than those isolated from cancer patients.

REFERENCES 1. (1998). Mastectomy or lumpectomy? The choice of operation for clinical stages I and II breast cancer. The Steering Committee on Clinical Practice Guidelines for the Care and Treatment of Breast Cancer. Canadian Association of Radiation Oncologists. CMAJ 158 Suppl 3, S15-21.
2. Alarcon-Segovia, D. (2001). The recovery of self tolerance in SLE. Lupus 10, 521-522.
3. Alarcon-Segovia, D., Ruiz-Arguelles, A., and Fishbein, E. (1978). Antibody to nuclear ribonucleoprotein penetrates live human mononuclear cells through Fc receptors. Nature 271, 67-69.
4. Allison, K. H. (2012). Molecular pathology of breast cancer: what a pathologist needs to know. Am J Clin Pathol 138, 770-780.
5. Avrameas, S. (1991). Immunol Today 12, 154-159.
6. Bernatsky, S., Ramsey-Goldman, R., Foulkes, W. D., Gordon, C., and Clarke, A. E. (2011). Breast, ovarian, and endometrial malignancies in systemic lupus erythematosus: a meta-analysis. Br J Cancer 104, 1478-1481.
7. Berry, D. A., Cronin, K. A., Plevritis, S. K., Fryback, D. G., Clarke, L., Zelen, M., Mandelblatt, J. S., Yakovlev, A. Y., Habbema, J. D., and Feuer, E. J. (2005). Effect of screening and adjuvant therapy on mortality from breast cancer. N Engl J Med 353, 1784-1792.
8. Blixt, O., Bueti, D., Burford, B., Allen, D., Julien, S., Hollingsworth, M., Gammerman, A., Fentiman, I., and Burchell, J. M. (2011). Autoantibodies to aberrantly glycosylated MUC1 in early stage breast cancer are associated with a better prognosis. Breast Cancer Res 13, R25.
9. Burnet, M. (1957). Cancer: a biological approach. III. Viruses associated with neoplastic conditions. IV. Practical applications. Br Med J 1, 841-847.
10. Chaffer, C. L., and Weinberg, R. A. (2011). A perspective on cancer cell metastasis. Science 331, 1559-1564.
11. Cheung, K. J., Gabrielson, E., Werb, Z., and Ewald, A. J. (2013). Collective invasion in breast cancer requires a conserved basal epithelial program. Cell 155, 1639-1651.
12. Chinoy, H., Salway, F., John, S., Fertig, N., Tait, B. D., Oddis, C. V., Ollier, W. E., and Cooper, R. G. (2007). Interferon-gamma and interleukin-4 gene polymorphisms in Caucasian idiopathic inflammatory myopathy patients in UK. Ann Rheum Dis 66, 970-973.
13. Cohen, I. R. (2000). Discrimination and dialogue in the immune system. Semin Immunol 12, 215-219; discussion 257-344.
14. Cohen, I. R., and Cooke, A. (1986). Natural autoantibodies might prevent autoimmune disease. Immunol Today 7, 363-364.
15. Cooper, G. S., Germolec, D., Heindel, J., and Selgrade, M. (1999). Linking environmental agents and autoimmune diseases. Environ Health Perspect 107 Suppl 5, 659-660.
16. Coutinho, A., Kazatchkine, M. D., and Avrameas, S. (1995). Natural autoantibodies. Curr Opin Immunol 7, 812-818.
17. Daffa, N. I., Tighe, P. J., Come, J. M., Fairclough, L. C., and Todd, I. (2015). Natural and disease-specific autoantibodies in chronic obstructive pulmonary disease. Clin Exp Immunol 180, 155-163.
18. Danke, N. A., Koelle, D. M., Yee, C., Beheray, S., and Kwok, W. W. (2004). Autoreactive T cells in healthy individuals. J Immunol 172, 5967-5972.
19. Dunn, G. P., Bruce, A. T., Ikeda, H., Old, L. J., and Schreiber, R. D. (2002). Cancer immunoediting: from immunosurveillance to tumor escape. Nat Immunol 3, 991-998.
20. Ehrenstein, M. R., and Notley, C. A. (2010). The importance of natural IgM: scavenger, protector and regulator. Nat Rev Immunol 10, 778-786.
21. Encinas, J. A., and Kuchroo, V. K. (2000). Mapping and identification of autoimmunity genes. Curr Opin Immunol 12, 691-697.
22. Ewald, A. J., Brenot, A., Duong, M., Chan, B. S., and Werb, Z. (2008). Collective epithelial migration and cell rearrangements drive mammary branching morphogenesis. Dev Cell 14, 570-581.
23. Filion, M. C., Proulx, C., Bradley, A. J., Devine, D. V., Sekaly, R. P., Decary, F., and Chartrand, P. (1996). Presence in peripheral blood of healthy individuals of autoreactive T cells to a membrane antigen present on bone marrow-derived cells. Blood 88, 2144-2150.
24. Fiorentino, D. F., Chung, L. S., Christopher-Stine, L., Zaba, L., Li, S., Mammen, A. L., Rosen, A., and Casciola-Rosen, L. (2013). Most patients with cancer-associated dermatomyositis have antibodies to nuclear matrix protein NXP-2 or transcription intermediary factor 1gamma. Arthritis Rheum 65, 2954-2962.
25. Fleming, J. N., and Schwartz, S. M. (2008). The pathology of scleroderma vascular disease. Rheum Dis Clin North Am 34, 41-55; vi.
26. Friedl, P., Locker, J., Sahai, E., and Segall, J. E. (2012). Classifying collective cancer cell invasion. Nat Cell Biol 14, 777-783.
27. Furst, D. E., Amato, A. A., Iorga, S. R., Bancroft, T., and Fernandes, A. W. (2012). Medical costs and health-care resource use in patients with inflammatory myopathies in an insured population. Muscle Nerve 46, 496-505.
28. Golan, T. D., Gharavi, A. E., and Elkon, K. B. (1993). Penetration of autoantibodies into living epithelial cells. J Invest Dermatol 100, 316-322.
29. Grabar, P. (1975). Hypothesis. Auto-antibodies and immunological theories: an analytical review. Clin Immunol Immunopathol 4, 453-466.
30. Hanahan, D., and Weinberg, R. A. (2011). Hallmarks of cancer: the next generation. Cell 144, 646-674.
31. Hansen, J. E., Chan, G., Liu, Y., Hegan, D. C., Dalal, S., Dray, E., Kwon, Y., Xu, Y., Xu, X., Peterson-Roth, E., et al. (2012). Targeting cancer with a lupus autoantibody. Sci Transl Med 4, 157ra142.
32. Hill, C. L., Zhang, Y., Sigurgeirsson, B., Pukkala, E., Mellemkjaer, L., Airio, A., Evans, S. R., and Felson, D. T. (2001). Frequency of specific cancer types in dermatomyositis and polymyositis: a population-based study. Lancet 357, 96-100.
33. Invernizzi, P. (2007). The X chromosome in female-predominant autoimmune diseases. Ann N Y Acad Sci 1110, 57-64.
34. Ippolito, A., Wallace, D. J., Gladman, D., Fortin, P. R., Urowitz, M., Werth, V., Costner, M., Gordon, C., Alarcon, G. S., Ramsey-Goldman, R., et al. (2011). Autoantibodies in systemic lupus erythematosus: comparison of historical and current assessment of seropositivity. Lupus 20, 250-255.
35. Jemal, A., Siegel, R., Xu, J., and Ward, E. (2010). Cancer statistics, 2010. CA Cancer J Clin 60, 277-300.
36. Joseph, C. G., Darrah, E., Shah, A. A., Skora, A. D., Casciola-Rosen, L. A., Wigley, F. M., Boin, F., Fava, A., Thoburn, C., Kinde, I., et al. (2014). Association of the autoimmune disease scleroderma with an immunologic response to cancer. Science 343, 152-157.
37. Kyewski, B., and Klein, L. (2006). A central role for central tolerance. Annu Rev Immunol 24, 571-606.
38. Lacroix-Desmazes, S., Kaveri, S. V., Mouthon, L., Ayouba, A., Malanchere, E., Coutinho, A., and Kazatchkine, M. D. (1998). Self-reactive antibodies (natural autoantibodies) in healthy individuals. J Immunol Methods 216, 117-137.
39. Leighton, J., Kalla, R. L., Turner, J. M., Jr., and Fennell, R. H., Jr. (1960). Pathogenesis of tumor invasion. II. Aggregate replication. Cancer Res 20, 575-586.
40. Lu, J., Steeg, P. S., Price, J. E., Krishnamurthy, S., Mani, S. A., Reuben, J., Cristofanilli, M., Dontu, G., Bidaut, L., Valero, V., et al. (2009). Breast cancer metastasis: challenges and opportunities. Cancer Res 69, 4951-4953.
41. Madrid, F. F., and Maroun, M. C. (2011). Serologic laboratory findings in malignancy. Rheum Dis Clin North Am 37, 507-525.
42. Mammen, A. L. (2010). Dermatomyositis and polymyositis: Clinical presentation, autoantibodies, and pathogenesis. Ann N Y Acad Sci 1184, 134-153.
43. Mathe, G. (1987). Passive, adoptive, and active immunotherapy: a review of clinical trials in cancer. Cancer Detect Prev Suppl 1, 279-290.
44. Mayes, M. D., Lacey, J. V., Jr., Beebe-Dimmer, J., Gillespie, B. W., Cooper, B., Laing, T. J., and Schottenfeld, D. (2003). Arthritis Rheum 48, 2246-2255.
45. Melero, J., Tarrago, D., Nunez-Roldan, A., and Sanchez, B. (1997). Human polyreactive IgM monoclonal antibodies with blocking activity against self-reactive IgG. Scand J Immunol 45, 393-400.
46. Miller, W. R. (2004). Biological rationale for endocrine therapy in breast cancer. Best Pract Res Clin Endocrinol Metab 18, 1-32.
47. Muramatsu, M., Sankaranand, V. S., Anant, S., Sugai, M., Kinoshita, K., Davidson, N. O., and Honjo, T. (1999). Specific expression of activation-induced cytidine deaminase (AID), a novel member of the RNA-editing deaminase family in germinal center B cells. J Biol Chem 274, 18470-18476.
48. Nguyen-Ngoc, K. V., Cheung, K. J., Brenot, A., Shamir, E. R., Gray, R. S., Hines, W. C., Yaswen, P., Werb, Z., and Ewald, A. J. (2012). ECM microenvironment regulates collective migration and local dissemination in normal and malignant mammary epithelium. Proc Natl Acad Sci USA 109, E2595-2604.
49. Noble, P. W., Young, M. R., Bernatsky, S., Weisbart, R. H., and Hansen, J. E. (2014). A nucleolytic lupus autoantibody is toxic to BRCA2-deficient cancer cells. Sci Rep 4, 5958.
50. Noseworthy, J. H., Lucchinetti, C., Rodriguez, M., and Weinshenker, B. G. (2000). Multiple sclerosis. N Engl J Med 343, 938-952.
51. Ochsenbein, A. F., Fehr, T., Lutz, C., Suter, M., Brombacher, F., Hengartner, H., and Zinkernagel, R. M. (1999). Control of early viral and bacterial distribution and disease by natural antibodies. Science 286, 2156-2159.
52. Pardoll, D. M. (2012). Immunology beats cancer: a blueprint for successful translation. Nat Immunol 13, 1129-1132.
53. Parish, C. R. (2003). Cancer immunotherapy: the past, the present and the future. Immunol Cell Biol 81, 106-113.
54. Sahai, E. (2007). Illuminating the metastatic process. Nat Rev Cancer 7, 737-749.
55. Schreiber, R. D., Old, L. J., and Smyth, M. J. (2011). Cancer immunoediting: integrating immunity's roles in cancer suppression and promotion. Science 331, 1565-1570.
56. Seddon, B., and Mason, D. (2000). The third function of the thymus. Immunol Today 21, 95-99.
57. Seidel, U. J., Schlegel, P., and Lang, P. (2013). Natural killer cell mediated antibody-dependent cellular cytotoxicity in tumor immunotherapy with therapeutic antibodies. Front Immunol 4, 76.
58. Shah, A. A., Hummers, L. K., Casciola-Rosen, L., Visvanathan, K., Rosen, A., and Wigley, F. M. (2015). Examination of autoantibody status and clinical features associated with cancer risk and cancer-associated scleroderma. Arthritis Rheumatol 67, 1053-1061.
59. Shah, A. A., Rosen, A., Hummers, L., Wigley, F., and Casciola-Rosen, L. (2010). Close temporal relationship between onset of cancer and scleroderma in patients with RNA polymerase I/III antibodies. Arthritis Rheum 62, 2787-2795.
60. Shamir, E. R., and Ewald, A. J. (2014). Three-dimensional organotypic culture: experimental models of mammalian biology and disease. Nat Rev Mol Cell Biol 15, 647-664.
61. Simian, M., Hirai, Y., Navre, M., Werb, Z., Lochter, A., and Bissell, M. J. (2001). The interplay of matrix metalloproteinases, morphogens and growth factors is necessary for branching of mammary epithelial cells. Development 128, 3117-3131.
62. Sinha, A. A., Lopez, M. T., and McDevitt, H. O. (1990). Autoimmune diseases: the failure of self tolerance. Science 248, 1380-1388.
63. Somers, E. C., Marder, W., Cagnoli, P., Lewis, E. E., DeGuire, P., Gordon, C., Helmick, C. G., Wang, L., Wing, J. J., Dhar, J. P., et al. (2014). Population-based incidence and prevalence of systemic lupus erythematosus: the Michigan Lupus Epidemiology and Surveillance program. Arthritis Rheumatol 66, 369-378.
64. Soussi, T. (2000). p 53 Antibodies in the sera of patients with various types of cancer: a review. Cancer Res 60, 1777-1788.
65. Street, S. E., Cretney, E., and Smyth, M. J. (2001). Perforin and interferon-gamma activities independently control tumor initiation, growth, and metastasis. Blood 97, 192-197.
66. Stutman, O. (1975). Immunodepression and malignancy. Adv Cancer Res 22, 261-422.
67. Tevaarwerk, A. J., Gray, R. J., Schneider, B. P., Smith, M. L., Wagner, L. I., Fetting, J. H., Davidson, N., Goldstein, L. J., Miller, K. D., and Sparano, J. A. (2013). Survival in patients with metastatic recurrent breast cancer after adjuvant chemotherapy: little evidence of improvement over the past 30 years. Cancer 119, 1140-1148.
68. Tinoco, G., Warsch, S., Gluck, S., Avancha, K., and Montero, A. J. (2013). Treating breast cancer in the 21st century: emerging biological therapies. J Cancer 4, 117-132.
69. Tomer, Y., and Shoenfeld, Y. (1988). The significance of natural autoantibodies. Immunol Invest 17, 389-424.
70. Vargo-Gogola, T., and Rosen, J. M. (2007). Modelling breast cancer: one size does not fit all. Nat Rev Cancer 7, 659-672.
71. Walker, L. S., and Abbas, A. K. (2002). The enemy within: keeping self-reactive T cells at bay in the periphery. Nat Rev Immunol 2, 11-19.

What is claimed is:

1. A method for identifying one or more antibodies that inhibit a cancer cell in vitro, the method comprising:
isolating blood from a subject afflicted with scleroderma;
purifying the one or more antibodies from the blood;
assaying in vitro the growth, viability, or mobility of a cancer cell in the presence of the one or more antibodies, wherein a reduction in the growth, viability, or mobility of the cancer cell in the presence of the one or more antibodies, as compared to the growth, viability or mobility of the cancer cell in the absence of the one or more antibodies, identifies the one or more antibodies as inhibiting the cancer cell;

wherein the subject afflicted with scleroderma is not afflicted with cancer; and wherein the growth, viability, or mobility of the cancer cell is reduced to a greater degree than would be observed when the cancer cell is assayed in the presence of a reference antibody obtained from a reference subject that is afflicted with scleroderma, wherein the reference subject is afflicted with cancer.

2. The method of claim 1, wherein purifying the one or more antibodies from the blood comprises purifying one or more IgG antibodies.

3. The method of claim 1, wherein the assayed cancer cell is a lung cancer cell, a breast cancer cell, a colon cancer cell, a pancreatic cancer cell, a renal cancer cell, a stomach cancer cell, a liver cancer cell, a bone cancer cell, a hematological cancer cell, a neural tissue cancer cell, a melanoma cell, a thyroid cancer cell, a ovarian cancer cell, a testicular cancer cell, a prostate cancer cell, a cervical cancer cell, a vaginal cancer cell, a or bladder cancer.

4. The method of claim 3, wherein the assayed cancer cell is a breast cancer cell.

5. The method of claim 4, wherein the breast cancer cell is a human breast cancer cell.

6. The method of claim 4, wherein the human breast cancer cell is ER+/PR+/HER2−.

7. The method of claim 4, wherein the human breast cancer cell is isolated from a primary breast tumor.

8. The method of claim 1, wherein the one or more antibodies reduces growth of the cancer cell.

9. The method of claim 1, wherein the one or more antibodies reduces viability of the cancer cell.

10. The method of claim 1, wherein the one or more antibodies reduces mobility of the cancer cell.

11. The method of claim 1, wherein assaying the reduction in the growth, viability, or mobility in the presence of the one or more antibodies comprises use of one or more of immunofluorescence, DIC microscopy, or confocal microscopy.

12. The method of claim 1, wherein the cancer cell is present in an embedded organoid.

13. The method of claim 1, wherein the blood from the subject afflicted with scleroderma is fresh.

14. The method of claim 1, wherein the blood from the subject afflicted with scleroderma is frozen.

15. The method of claim 1, wherein the assaying step is run in the absence of a stromal cell population.

16. The method of claim 1, wherein the assaying step is run in the presence of a stromal cell population.

17. The method of claim 16, wherein the stromal cell population comprises fibroblasts.

\* \* \* \* \*